United States Patent
Muse et al.

(10) Patent No.: US 11,684,765 B2
(45) Date of Patent: Jun. 27, 2023

(54) BIDIRECTIONAL MEDICAL VALVES

(71) Applicant: Piper Access, LLC, Salt Lake City, UT (US)

(72) Inventors: Jay Allen Muse, Salt Lake City, UT (US); Kevin Jerry Cook, Kaysville, UT (US)

(73) Assignee: Piper Access, LLC, Salt Lake City, UT (US)

( * ) Notice: Subject to any disclaimer, the term of this patent is extended or adjusted under 35 U.S.C. 154(b) by 622 days.

(21) Appl. No.: 16/697,156

(22) Filed: Nov. 26, 2019

(65) Prior Publication Data

US 2020/0197683 A1 Jun. 25, 2020

Related U.S. Application Data

(60) Provisional application No. 62/771,375, filed on Nov. 26, 2018.

(51) Int. Cl.
*A61M 39/06* (2006.01)
*A61M 39/02* (2006.01)
(Continued)

(52) U.S. Cl.
CPC .... *A61M 39/0613* (2013.01); *A61M 39/0247* (2013.01); *A61M 39/225* (2013.01);
(Continued)

(58) Field of Classification Search
CPC .......... A61M 39/0613; A61M 39/0247; A61M 39/225; A61M 2039/027;
(Continued)

(56) References Cited

U.S. PATENT DOCUMENTS 4,143,853 A * 3/1979 Abramson ............ A61M 39/26
604/246
4,354,492 A * 10/1982 McPhee ................ F16K 15/023
604/247
(Continued)

FOREIGN PATENT DOCUMENTS

| EP | 0 474 069 B1 | 10/1995 |
|---|---|---|
| WO | 2014153302 A1 | 9/2014 |
| WO | 2020112915 A1 | 6/2020 |

OTHER PUBLICATIONS

European Patent Office, Extended European Search Report in European Patent Application No. 19890202.5, dated Oct. 31, 2022 (7 pages).

(Continued)

*Primary Examiner* — Lauren P Farrar
*Assistant Examiner* — Hamza A Darb
(74) *Attorney, Agent, or Firm* — Med Venture Management, LLC; Daniel C. Higgs

(57) ABSTRACT

A medical valve can include a housing that includes a sidewall and defines a chamber. The medical valve can include a septum coupled to the housing. The septum can include a proximal surface and a selectively openable closure positioned within the chamber. The medical valve can further include a plurality of projections that extend away from the sidewall and are configured to contact the proximal surface of the septum to oppose movement of a restricted portion of the septum in a proximal direction such that an aspiration cracking pressure required to open the closure to permit fluid flow through the septum in the proximal direction exceeds an infusion cracking pressure required to open the closure to permit fluid flow through the septum in the distal direction.

24 Claims, 24 Drawing Sheets

(51) Int. Cl.
*A61M 39/22* (2006.01)
*A61M 39/10* (2006.01)

(52) U.S. Cl.
CPC . *A61M 2039/027* (2013.01); *A61M 2039/064* (2013.01); *A61M 2039/066* (2013.01); *A61M 2039/1072* (2013.01)

(58) Field of Classification Search
CPC ...... A61M 2039/064; A61M 2039/066; A61M 2039/1072; A61M 2039/242; A61M 2039/2426; A61M 39/223; A61M 39/24; A61M 25/10185; A61M 2039/0036; A61M 2039/2473; A61M 39/22; A61B 5/15003; A61B 5/150221; A61B 5/150992
See application file for complete search history.

(56) References Cited

U.S. PATENT DOCUMENTS

| | | | |
|---|---|---|---|
| 4,946,448 A | 8/1990 | Richmond | |
| 5,205,834 A | 4/1993 | Moorehead et al. | |
| 5,242,413 A | 9/1993 | Heiliger | |
| 6,344,033 B1 | 2/2002 | Jepson et al. | |
| D644,731 S | 9/2011 | Fangrow, Jr. | |
| 8,123,726 B2 * | 2/2012 | Searfoss | A61M 39/0606 604/167.04 |
| 2005/0010176 A1 | 1/2005 | Dikeman et al. | |
| 2007/0163664 A1 | 7/2007 | Mijers et al. | |
| 2011/0087093 A1 | 4/2011 | Buiser | |
| 2013/0338608 A1 * | 12/2013 | Moorehead | A61M 39/24 604/246 |
| 2016/0129181 A1 | 5/2016 | Mijers et al. | |
| 2018/0043149 A1 | 2/2018 | Martin | |

OTHER PUBLICATIONS

International Searching Authority, Notification of Transmittal of the International Search Report and the Written Opinion of the International Searching Authority in International Application No. PCT/US2019/063466, dated Apr. 14, 2020, 14 pages.

International Searching Authority, International Preliminary Report on Patentability in International Application No. PCT/US2019/063466, dated May 25, 2021, 10 pages.

* cited by examiner

BIDIRECTIONAL MEDICAL VALVES

CROSS-REFERENCE TO RELATED APPLICATIONS

This application claims the benefit under 35 U.S.C. § 119(e) of U.S. Provisional Patent Application No. 62/771,375, filed on Nov. 26, 2018, titled BIDIRECTIONAL MEDICAL VALVES, the entire contents of which are hereby incorporated by reference herein.

TECHNICAL FIELD

Certain embodiments described herein relate generally to valves, and further embodiments relate more particularly to bidirectional medical valves, such as may be used, for example, with catheters, such as peripherally inserted central catheters (PICCs).

BACKGROUND

Certain medical valves are used to permit fluid flow in either a first direction, such as for infusion through the valve, or a second direction, such as for aspiration through the valve. Known bidirectional medical valves, however, suffer from one or more drawbacks. Various limitations of such bidirectional medical valves can be resolved, remedied, ameliorated, or avoided by certain embodiments described herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
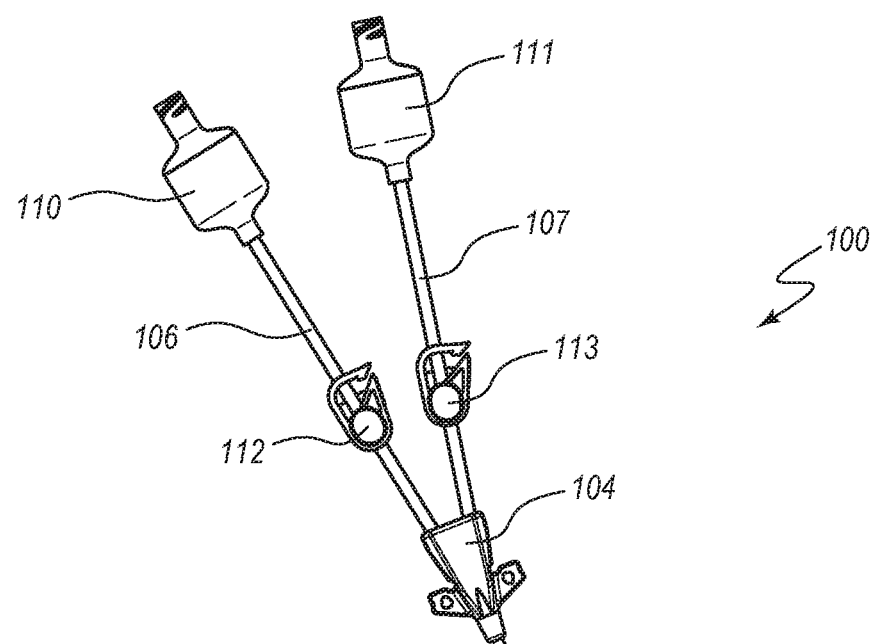
FIG. 1 is a perspective view of an embodiment of a dual lumen peripherally inserted central catheter (PICC) that includes a pair of medical valves, each valve being in fluid communication with a separate lumen of a catheter shaft, and each valve being an embodiment of a bidirectional medical valve that permits fluid flow through the valve in either an infusion direction or an aspiration direction.

The present disclosure relates generally to valves, and more particularly relates to bidirectional valves. Certain embodiments of valves disclosed herein can be particularly useful for a variety of medical applications. For example, embodiments of the valves may be particularly well suited for use in applications in which different cracking pressures in opposite directions of fluid flow are desired. In some instances, the valves can be used advantageously with catheters via which fluids are infused into a patient and/or via which blood is drawn or aspirated from the patient. Certain embodiments may perform well at flushing blood from the bidirectional valve after blood draws have been taken through the valve. In some embodiments, the valves may further be suitable for power injection. For example, certain valves may be used as proximal valves in PICC catheters, such as power injectable PICC catheters. These and other advantages will be evident from the present disclosure.

Proximal valves for PICC catheters are known in the art. Proximal valves generally are coupled to the proximal ends of catheter assemblies in which a catheter body is insertable into a body of a patient, and the valves remain at an exterior of the patient when the catheter body is in place within the patient to provide access to one or more lumens of the catheter. Such proximal valves generally can be used to infuse one or more fluids into a patient and/or to aspirate blood or other fluids from the patient. Known proximal valves, however, suffer from a variety of drawbacks.

For example, some known proximal valves include geometries, architectures, or internal configurations that inhibit blood and/or microbes from being flushed from the valves. In some instances, blood that is drawn into a proximal chamber of the valve during aspiration can enter between a shelf-like feature within a housing of the valve and a septum. Upon subsequent infusion through the valve, at least some of the blood can become trapped in this region, as fluid dynamics of the pressurized infusion fluid act to maintain at least some of the trapped blood in place, or push it further into crevices between adjacent surfaces, rather than clear the blood from this region. Stated otherwise, the shelf-like feature does not permit fluid to get in between the septum and the shelf-like feature, thereby trapping blood between these components. Similarly, microbes within the valve can be urged into such regions and permitted to colonize, rather than being flushed out.

In other or further instances, known proximal valves suffer from significant variation in one or more cracking pressures. The term "cracking pressure" is used herein in its ordinary sense, and includes, for example, a pressure differential across a feature at which a closure in that feature opens to permit fluid to flow through the closure. The term "closure" is used herein in its ordinary sense, and includes, for example, any suitable feature that can be closed and/or selectively opened. Thus, the term "closure" is not meant to imply a feature that is permanently closed, but rather, a feature that can be in a closed configuration to prevent fluid flow therethrough and may be transitioned to an open configuration to permit fluid flow therethrough. In some embodiments, a closure may be biased toward the closed configuration, and this bias may be overcome to open the closure. In other embodiments, the closure may be biased toward the open configuration, and this bias may be overcome to close the closure.

Certain known proximal valves may suffer from inconsistent infusion cracking pressures and/or inconsistent aspiration cracking pressures from one valve to the next, despite manufacturers' attempts to produce substantially identical or consistent valves. For example, one known bidirectional proximal valve includes an elastomeric septum that includes three closures. To permit fluid flow through the valve in one direction, a first of the three closures opens while the second and third closures remain closed, whereas to permit fluid flow through the valve in the opposite direction, the second and third closures open and the first valve closes. The cracking pressure of the first closure and/or the cracking pressure (or pressures) of the second and third closures can be widely inconsistent from one valve to the next. These inconsistencies may result, for example, from minor variations in the thickness of the septum and/or variations in the hardness of the material from which the septum is fabricated from one valve to the next and/or from one manufacturing lot to the next.

Often, such proximal valves may be incorporated into catheter assemblies prior to determining that one or more cracking pressures are outside of the manufacturer's tolerances, and the catheter assemblies must then be discarded. This can lead to significant material waste and heightened manufacturing costs.

Further, inconsistent cracking pressures, or even cracking pressures that vary within a large range of "acceptable" values (as determined by a manufacturer), can lead to unreliable tactile feedback during use of the catheter assemblies. For example, practitioners in many instances use tactile feedback to determine whether infusion and/or aspiration through a catheter assembly requires greater pressure than expected. Practitioners can develop a sense for whether or not a catheter is occluded based on how easy or difficult it is to infuse or aspirate through the catheter. Variation in cracking pressures in the proximal valve, however, can make it difficult for practitioners to gain an accurate sense for when occlusions may be present. For example, in many instances, practitioners may inaccurately conclude that a catheter is occluded when, in fact, the aspiration or infusion through a proximal valve is merely more difficult, as compared with the proximal valves of other catheter assemblies, due to variation in the cracking pressures of the proximal valves.

In other or further instances, inconsistent cracking pressures and/or valve degradation or failure of known proximal valves may result from the presence of stylets or guidewires within the valves. For example, in some instances, catheter assemblies may be prepackaged with a stylet extending through a proximal valve. In some instances, a proximal valve may include a slit through which the stylet passes. Over time, the presence of the stylet may deform one or more adjacent contact surfaces of the slit such that the contact surfaces may not align properly to seal the slit. Thus, the proximal valve may no longer operate as designed.

Certain embodiments described herein address, ameliorate, resolve, or avoid one or more of the foregoing disadvantages of known proximal valves. For example, various embodiments disclosed herein are configured to more effectively flush blood from a proximal chamber, to be manufactured with consistent and repeatable cracking pressures, and/or to be prepackaged with stylets extending therethrough or to permit guidewires to be passed therethrough without any degradation in valving performance. Various embodiments, can achieve one or more of these and/or other advantages, including those expressly discussed herein and those otherwise apparent from the present disclosure.

FIG. 1 depicts an embodiment of a catheter assembly 100 that includes a catheter body 102 (which may also be referred to as a catheter, catheter sheath, etc.), a junction 104, a pair of extension legs 106, 107, and a pair of proximal valves 110, 111 attached to the respective proximal ends of the extension legs 106, 107. The illustrated catheter body 102 includes two lumens (not shown), and each lumen is in fluid communication with a respective one of the extension legs 106, 107 and a respective one of the proximal valves 110, 111 via fluid channels (not shown) that extend through the junction 104. The catheter assembly 100 can further include a pair of clamps 112, 113: one for each extension leg 106, 107, respectively. In the illustrated embodiment, the two lumens through the catheter body 102 extend fully from a proximal end of the catheter body 102 to a distal end thereof. The lumens thus may terminate at a distal tip of the catheter body 102. Other suitable arrangements or configurations of the lumens are contemplated.

The catheter assembly 100 can be configured for any suitable use. In the illustrated embodiment, the catheter assembly 100 is suitable for use as a PICC. In some embodiments, the catheter assembly 100 and some or all components thereof, including the proximal valves 110, 111, may be suitable for power injections.

As used herein, the term "power injection" is consistent with the generally accepted definition of this term, and refers to pressurized infusions that occur at high flow rates, such as up to 4.0 mL/s or up to 5.0 mL/sec; that often involve injection of viscous materials, such as materials (e.g., contrast media) having a viscosity of 11.8 cP+/−0.3 cP; and that take place at elevated pressures. In like manner, a "power injectable" catheter assembly is one that is capable of sustaining power injection without leaking, bursting, or swelling to a size that is not usable within the vasculature. For example, a power injectable catheter assembly may be one that complies with the power injection specifications of the International Standards Organization (ISO) standard ISO 10555-1. Thus, for example, a power injectable PICC is a PICC configured to sustain power injections. In some instances, power injectable PICCs can be and/or remain operable at pressures of up to about 180, 190, 200, 210, 220, 230, 240, 250, or even 260 psi. In many instances, PICCs may also be used for other functions, such as intravenous therapy at lower pressures or standard infusion and aspiration or blood sampling.

In the illustrated embodiment, the proximal valves 110, 111 are substantially identical to each other. In other embodiments, the proximal valves 110, 111 may be different from each other. For example, the proximal valves 110, 111 may have different performance characteristics, such as with respect to power injectability and/or with respect to cracking pressures. In some instances, one of the proximal valves 110, 111 may be configured for power injections (e.g., can operate at and suffer little or no performance degradation due to elevated power injection pressures), whereas the other of the proximal valves 110, 111 may only be configured for operation at lower pressures.

In some embodiments, the catheter assembly 100 may include a stylet (see FIG. 18) that extends through the proximal valve 110, the extension leg 106, one of the fluid channels of the junction 104, and one of the lumens of the catheter body 102. In other or further embodiments, the stylet may instead extend through the other proximal valve 111 and its associated fluid path through the catheter assembly 100. For example, in some embodiments, the stylet may be inserted just prior to introducing the catheter assembly 100 into a patient. In other embodiments, the stylet may be prepackaged with the catheter assembly 100 so as to extend through one of the fluid paths of the catheter assembly 100. Embodiments of such catheter assemblies 100 that include a stylet can be used in manners known in the art, such as for stiffening the catheter body 102 for advancement through or otherwise positioning the catheter body 102 within the vasculature of a patient. Similarly, the catheter assembly 100 may be advanced over a guidewire in manners such as those known in the art.

In the illustrated embodiment, each proximal valve 110, 111 is a bidirectional valve. Stated otherwise, each proximal valve 110, 111 is configured to permit fluid to pass through the valve in each of a distal direction and a proximal direction. The direction of fluid flow may also be referred to as an ingress or infusion direction (e.g., toward or directed into the patient) or as an egress or aspiration direction (e.g., away from or directed out of the patient). As further discussed below, the bidirectional valves 110, 111 can be asymmetrical, such that a cracking pressure in one direction is different from a cracking pressure in the opposite direction. Stated otherwise, each valve 110, 111 is an asymmetric bidirectional valve. In the illustrated embodiment, the aspiration cracking pressure is higher than the infusion cracking pressure. It may be said that it is easier to introduce fluids into the patient through the proximal valves 110, 111 than it is to remove fluids from the patient through the proximal valves 110, 111.

Figure 2:
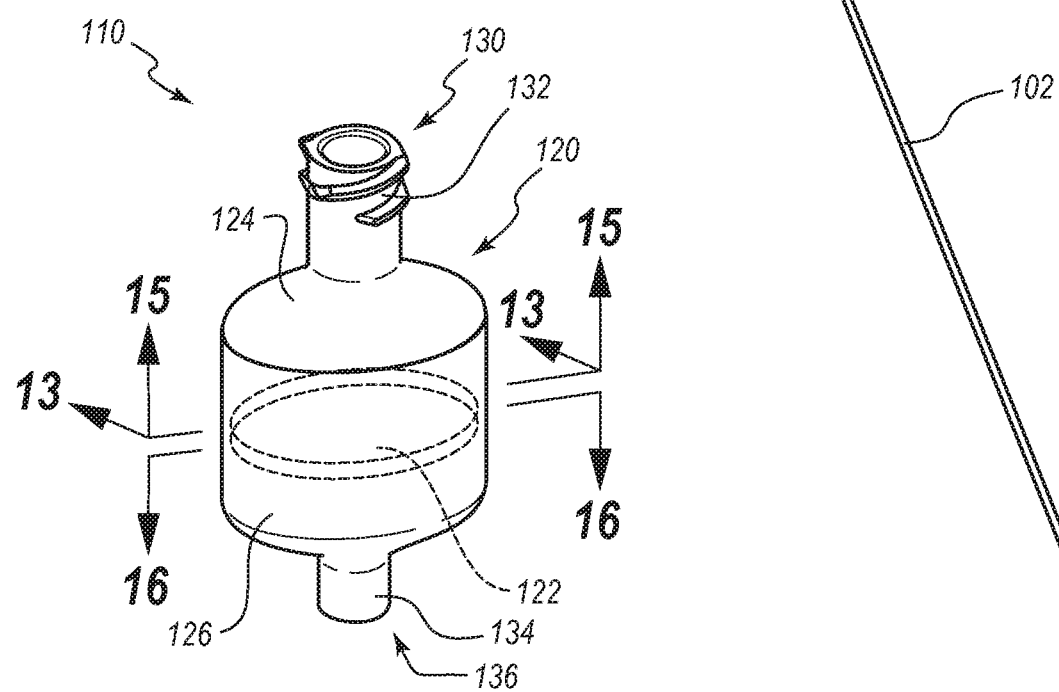
FIG. 2 is a perspective view of an embodiment of a bidirectional medical valve, such as either of the valves depicted in FIG. 1.
Figure 3:
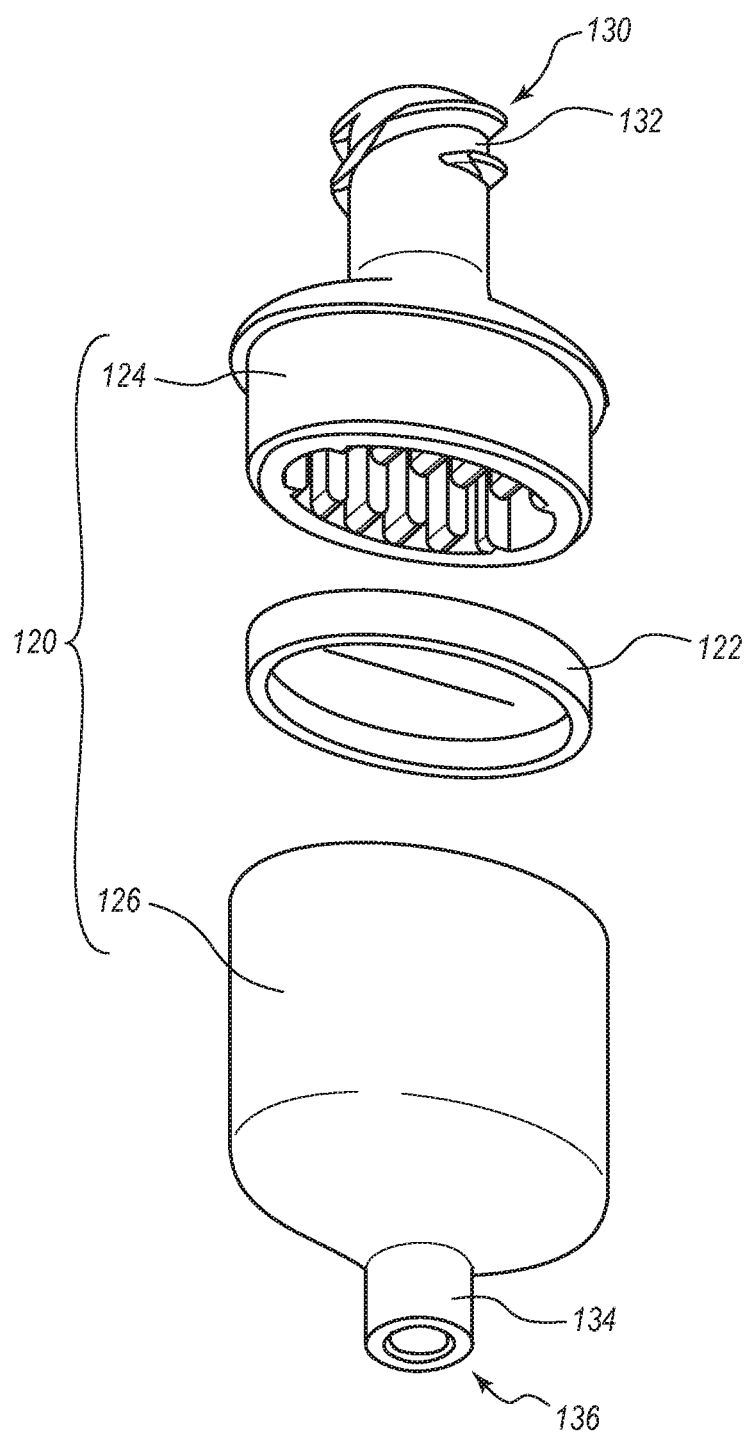
FIG. 3 is an exploded perspective view of the valve of FIG. 2.

FIGS. 2 and 3 depict an embodiment of the valve 110, which can include a housing 120 and a septum 122. The septum 122 may alternatively be referred to as a valve or as a valving member. In the illustrated embodiment, the housing 120 includes a plurality of pieces that are joined together. In particular, the housing 120 is a two-part housing that includes a first piece 124 and a second piece 126. The first and second pieces 124, 126 may also be referred to as separate housing members, elements, components, etc. In some embodiments (such as that depicted in FIG. 1), the housing member 124 may also be referred to as a proximal housing member, and the housing member 126 may also be referred to as a distal housing member. Other orientations of the housing members 124, 126 are contemplated, however, so the terms proximal and distal in this context is only illustrative and should not be construed as limiting. The housing members 124, 126 may be joined together in any suitable fashion, including (without limitation) via one or more of adhesive bonding, solvent bonding, ultrasonic welding, etc.

The septum 122 can be fixedly secured to the housing 120. For example, in the illustrated embodiment, the septum 122 is captured or held between the first and second housing member 124, 126, as further discussed below. In some instances, the septum 122 is gripped between the housing members 124, 126 without either housing member 124, 126 penetrating through the septum 122. In other or further embodiments, one or more of the housing members 124, 126 may pass through the septum 122 to retain or further retain the septum 122 in a desired position, such as discussed below, for example, with respect to FIGS. 18-30. Stated otherwise, the septum 122 may be anchored or otherwise securely attached to one or more of the housing members 124, 126, whether instead of or in addition to being gripped between the housing members 124, 126.

In the illustrated embodiment, each of the housing members 124, 126 has a substantially oval-shaped profile. Stated otherwise, a perimeter or transverse cross-sectional shape of each housing member 124, 126 is oval-shaped. The septum 122 likewise defines an oval-shaped profile or perimeter. Other shapes and configurations are contemplated.

The proximal housing member 124 can include a connection interface 130 that is configured to couple with one or more medical devices for infusion through the valve 110 in the ingress direction or for aspiration through the valve 110 in the egress direction. Stated otherwise, the connection interface 130 can permit infusion of fluid therethrough in the ingress direction and can permit aspiration of fluid therethrough in the egress direction. In the illustrated embodiment, the connection interface 130 comprises a Luer fitting 132. For example, in some instances, a first medical device (e.g., a syringe, a gravity feed intravenous fluid bag, a power injector, or any other suitable medical fluid delivery device) may be coupled with the Luer fitting 132 for purposes of infusing a medical fluid through the valve 110 and into a patient. In further instances, the same medical device (e.g., the syringe) may be used to aspirate a fluid (e.g., blood) from the catheter body 102 and/or the vasculature of the patient. The first medical device may be decoupled from and recoupled to the Luer fitting 132 between aspiration and/or infusion events. In other or further instances, the first medical device is decoupled from the Luer fitting 132 and a second medical device different from the first medical device is coupled with the Luer fitting 132 for aspiration. Any suitable medical devices are contemplated.

The distal housing member 126 can similarly include a connection interface 134. In the illustrated embodiment, the connection interface 134 comprises a protrusion or port 136 that is configured to be fixedly secured to a proximal end of an extension tube in any suitable manner, and generally in a fluid-tight manner. For example, in some embodiments, the distal housing member 126 can be overmolded onto an extension leg 106, 107. Other forms of attachment are also contemplated.

Figure 4:
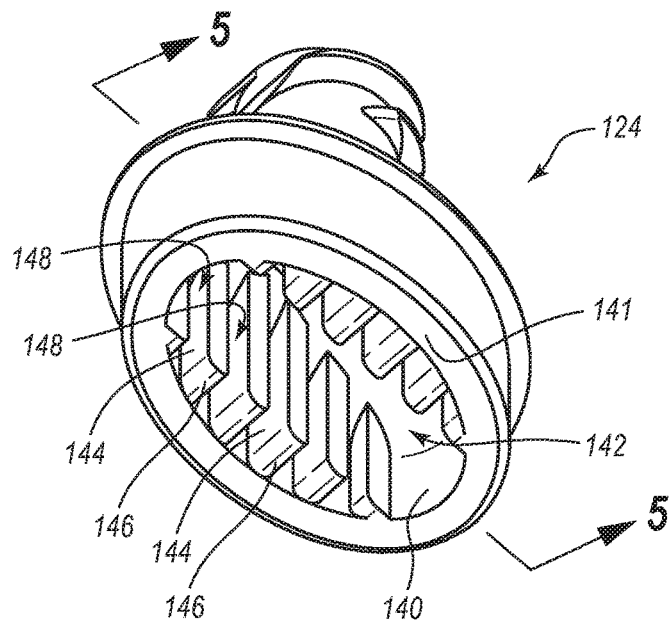
FIG. 4 is a bottom perspective view of an embodiment of a first housing piece of the valve of FIG. 2.
Figure 5:
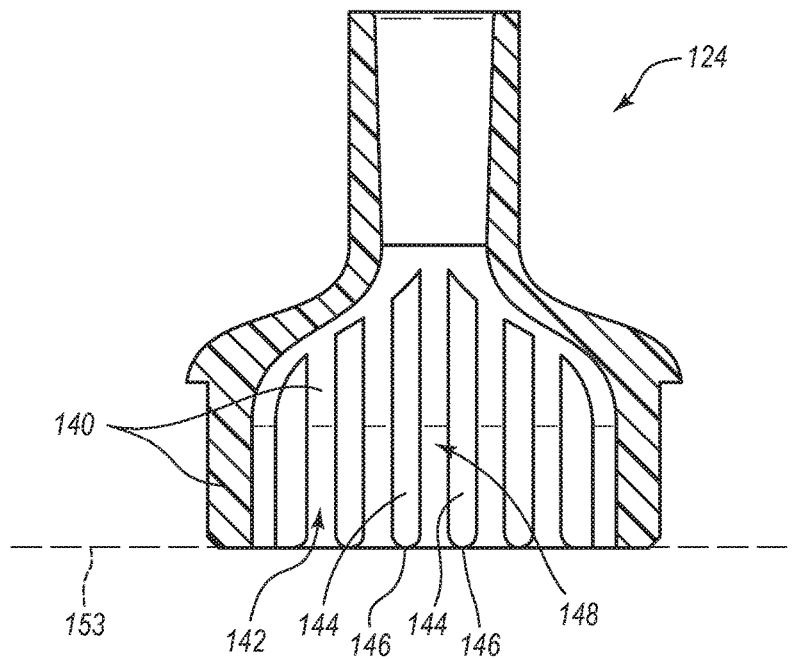
FIG. 5 is a cross-sectional view of the first housing piece taken along the view line 5-5 in FIG. 4.
Figure 6:
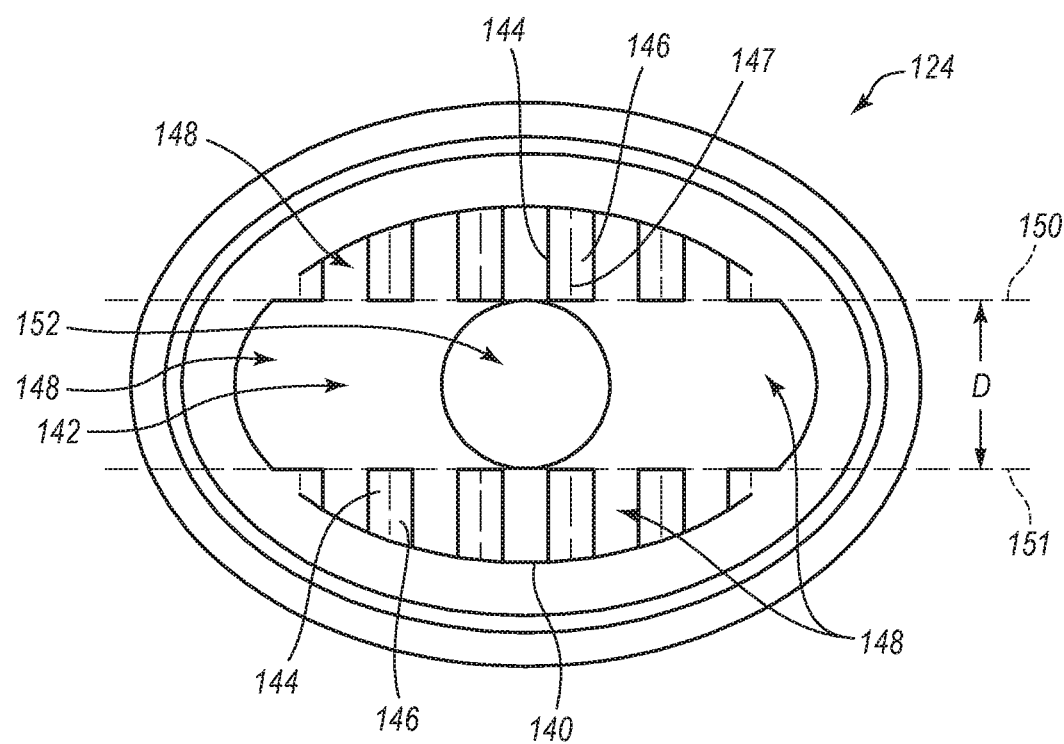
FIG. 6 is a bottom plan view of the first housing piece.

With reference to FIGS. 4-6, the proximal housing member 124 can include a sidewall 140 that defines a proximal chamber 142. The sidewall 140 can terminate at a distal face 141. The proximal housing member 124 can further include a plurality of support structures 144 that extend inwardly away from the sidewall 140 into the proximal chamber 142. In the illustrated embodiment, the support structures 144 may also be referred to as fins, ribs, elongated protrusions, etc. More generally, the support structures 144 may be referred to as projections. In the illustrated embodiment, the proximal housing member 124 includes 12 support structures 144.

The proximal housing member 124 can be formed in any suitable manner. In the illustrated embodiment, the proximal housing member 124, including the sidewall 140 and the support structures 144, is integrally formed of a unitary piece of material (e.g., via injection molding).

In the illustrated embodiment, each fin 144 defines a contact or restriction surface 146 at a distal end thereof. Moreover, each pair or adjacent fins 144 defines a fluid channel 148 therebetween. As further discussed below, the fins 144 can constrain movement of the fluid through the channels 148, or stated otherwise, can direct, channel, or guide fluid flow through the channels 148 toward the restriction surfaces 146. Such constrained or directed fluid flow through the fluid channels 148 can assist in flushing all surfaces in or defining the proximal chamber 142. The channels 148 may also be referred to as flushing channels. As shown in FIG. 6, the illustrated embodiment of the proximal housing member 124 includes 12 fluid channels 148. In particular, ten fluid channels 148 are shown as being elongated in the vertical direction, in the illustrated orientation, with five channels 128 being at the upper side of the housing member 124 and the other five channels 128 being at the lower side of the housing member 124. In addition, one fluid channel 148 is positioned at the left side of the housing member 124 between two small fins 144, and another fluid channel 148 is positioned at the right side of the housing member 124 between two small fins 144.

As discussed further below, the restriction surfaces 146 can be configured to oppose movement or deformation of one or more specific regions of the septum 122 in the proximal direction. In the illustrated embodiment, each restriction surface 146 includes a curved or rounded surface at a distal end thereof. In particular, for the intermediate or centrally located fins 144, the restriction surfaces 146 are each shaped substantially as hemicylinders of varying length, thus defining a substantially semicircular or U-shaped cross-section. For the four fins 144 located at each end of the two rows of fins 144, a portion (e.g., a radially inner portion) of the restriction surface 146 is curved or rounded, whereas another portion (e.g., a radially outer portion) of the restriction surface 146 is flat so as to be flush with a distal face of the proximal housing member 124.

Other shapes of the restriction surfaces are contemplated. For example, in some embodiments, each of at least some of the restriction surfaces 146 may be formed of two planar surfaces that meet at a line that extends along a lower edge of each surface. The restriction surfaces thus may be substantially V-shaped in cross-section.

With reference to FIG. 6, in the illustrated embodiment, each restriction surface 146 extends inwardly from the sidewall 140 and terminates at one of two longitudinal planes 150, 151. The fins 144 likewise each terminate at an interior end thereof at one of the two longitudinal planes 150, 151 (see FIG. 4). In the illustrated embodiment, the longitudinal planes 150, 151 are oriented parallel to each other. The planes 150, 151 are positioned at opposite ends of a proximal opening 152 defined by the proximal housing member 124. The longitudinal planes 150, 151 can be separated from each other by a distance D. As further discussed below, the distance D by which the planes 150, 151 are separated from each other can influence an aspiration cracking pressure of the valve 110.

With reference to FIG. 5, in the illustrated embodiment, each restriction surface 146 extends to and touches a lateral plane 153 that is orthogonal to the longitudinal planes 150, 151. Stated otherwise, only a distal end of each restriction surface 146 extends to the lateral plane 153. The distal ends of the restriction surfaces 146 thus are all coplanar in the illustrated embodiment. Due to the rounded, hemicylindrical shape of many of the restriction surfaces 146, the distal ends of these surfaces substantially define a straight line 147 along, or at the level of, the plane 153, as shown in FIG. 6. As further shown in FIG. 6, these straight lines 147 can be oriented substantially orthogonal to the longitudinal planes 150, 151. In may also be said that adjacent lines 147 are parallel to each other. In other embodiments, adjacent lines 147 may angle toward or away from one another. In various of such embodiments, the lines 147 of adjacent restriction surfaces 146 do not physically touch, but extended projections of the lines may intersect at an angle that is no greater than 10, 15, 30, or 45 degrees. Other arrangements are contemplated.

As further discussed below, a proximal surface of the septum 122 can be positioned substantially at the level of the transverse plane 153. Stated otherwise, in embodiments where an upper or proximal surface of the septum 122 is substantially planar, the proximal surface can define the transverse plane 153 (see FIG. 14).

Figures 7, 8:
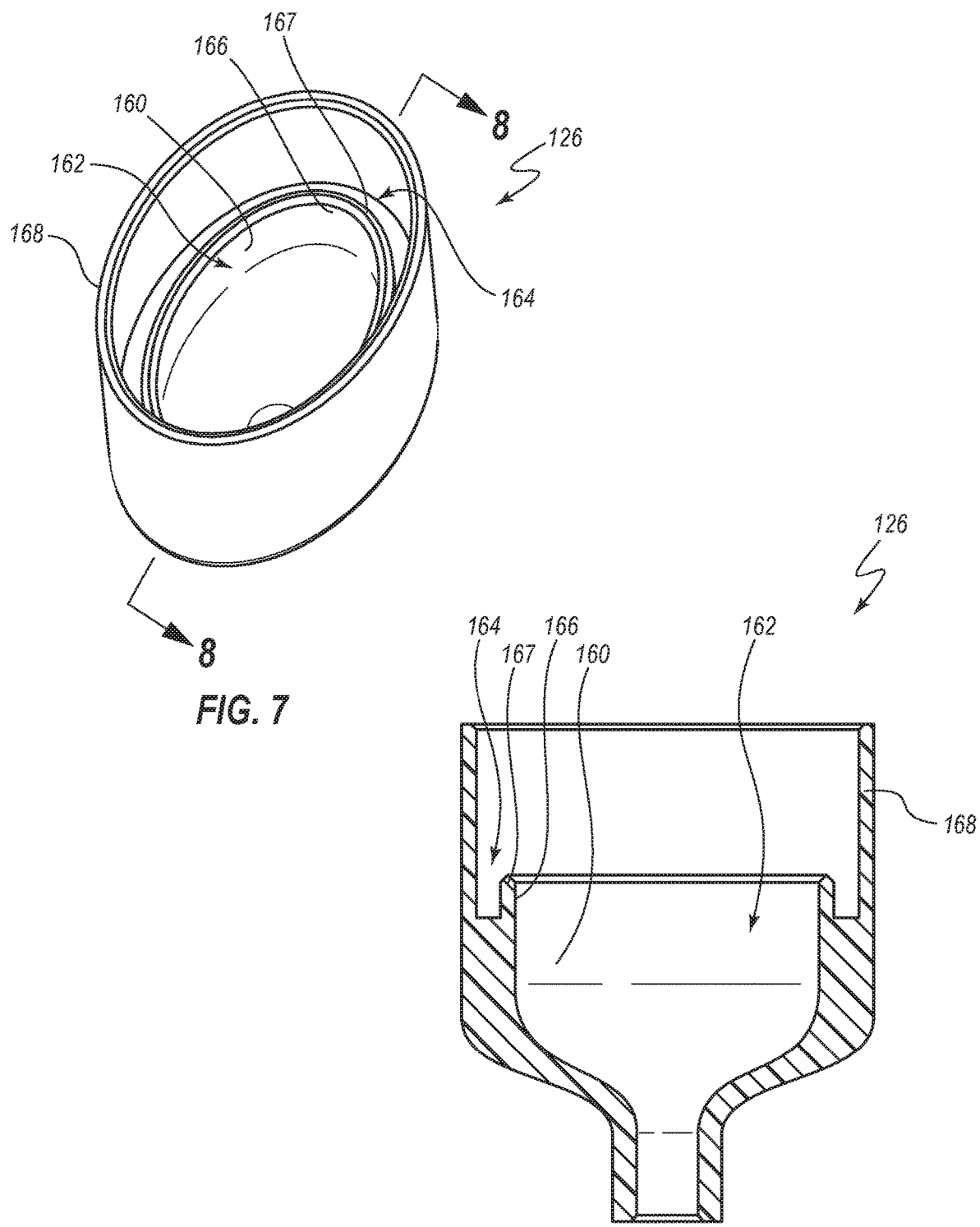
FIG. 7 is a top perspective view of an embodiment of a second housing piece of the valve of FIG. 2.
FIG. 8 is a cross-sectional view of the second housing piece taken along the view line 8-8 in FIG. 7.
Figure 9:
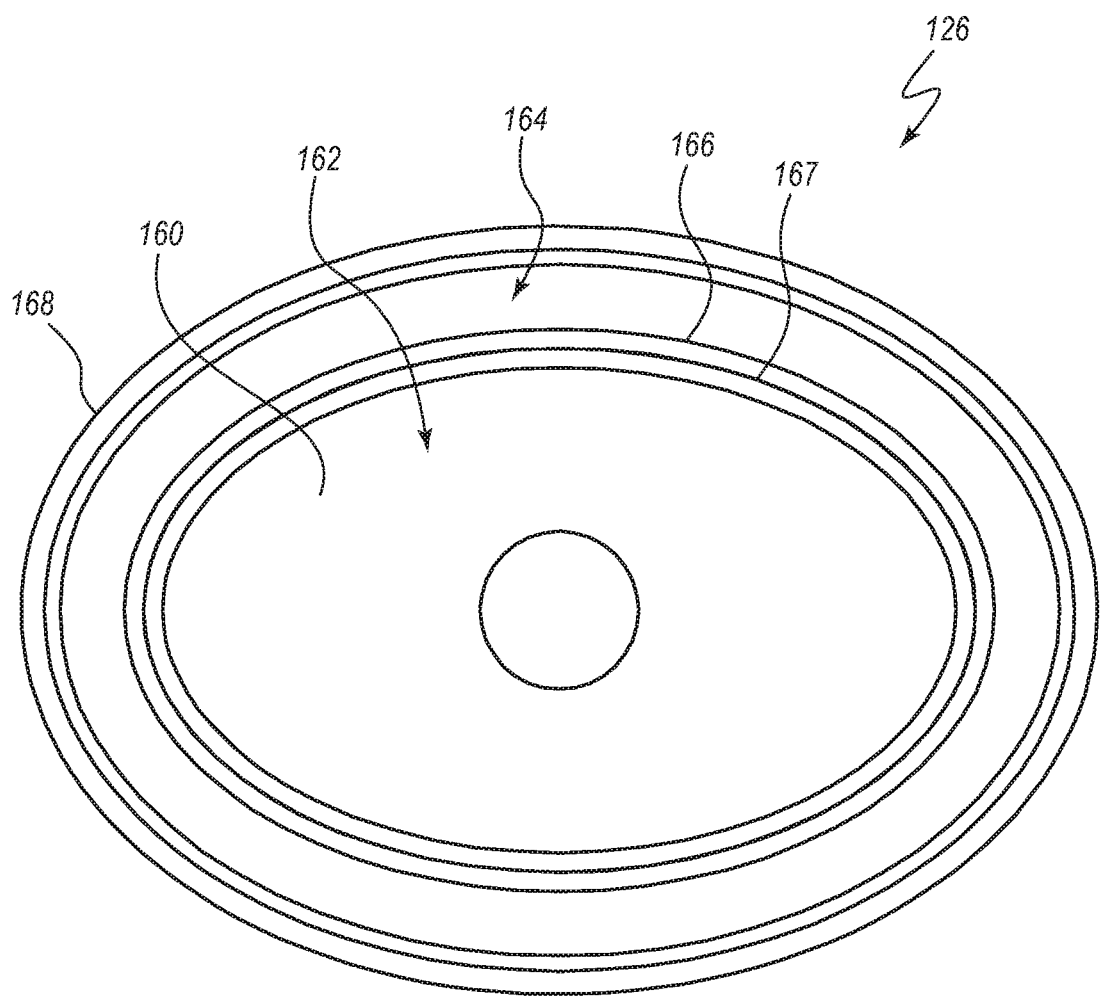
FIG. 9 is a top plan view of the second housing piece.

With reference to FIGS. 7-9, the distal housing member 126 includes a sidewall 160 (e.g., an inner sidewall) that defines a distal chamber 162. In the illustrated embodiment, the distal housing member 126 further includes an inner ridge or septum support 166 that extends about a full periphery of the distal chamber 162. The septum support 166 may define at least an upper end of the sidewall 160. A gripping and/or sealing rim 167 configured to engage the septum 122 can be positioned at the upper or proximal end of the septum support 166. In the illustrated embodiment, the sealing rim 167 is substantially V-shaped in cross-section (see FIG. 8).

The distal housing member 126 can include an outer sleeve 168 that can be positioned over and coupled with the proximal housing member 124. Any suitable attachment mechanism is contemplated, and is desirably fluid tight. In some embodiments, the outer sleeve 168 can be adhered or solvent bonded to the proximal housing member 124, and in further embodiments, the connection thus achieved can be fluid-tight, even at elevated pressures associated with power injections.

The distal housing member 126 can define a groove 164 or recess into which a downwardly projecting rim, lip, skirt, ring, edge, band, or flange of the septum 122 can be received, as discussed further below. An outer surface of the groove 164 can be defined by an inwardly facing surface of the outer sleeve 168, and an inner surface of the groove 164 can be defined by an outwardly facing surface of the septum support 166.

Figure 10:
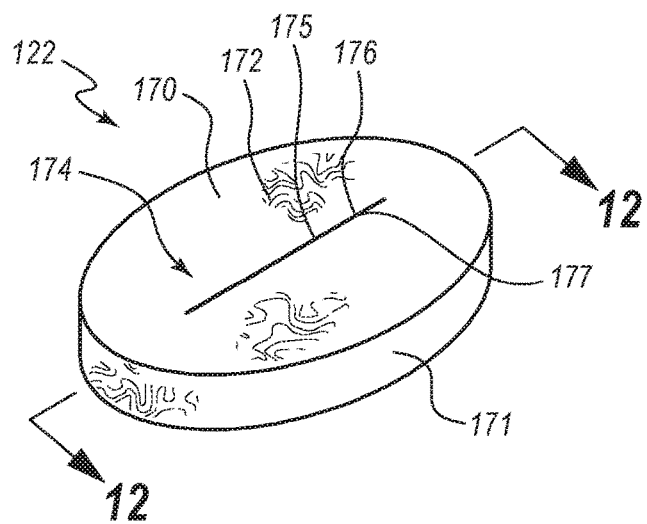
FIG. 10 is an upper perspective view of an embodiment of a septum of the valve of FIG. 2.
Figure 11:
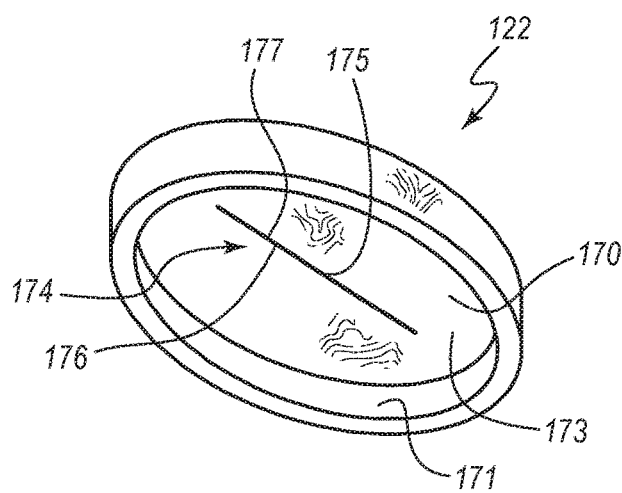
FIG. 11 is a lower perspective view of the septum.
Figure 12:
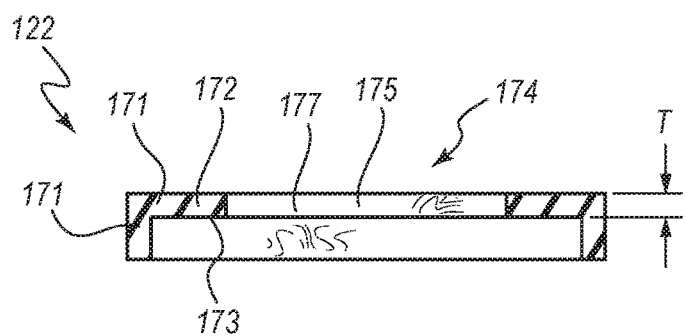
FIG. 12 is a cross-sectional view of the septum taken along the view line 12-12 in FIG. 10.

FIGS. 10-12 illustrate an embodiment of the septum 122, which can include a body 170 and a projecting rim, lip, skirt, ring, edge, band, or flange 171 that extends orthogonally from the body 170 around a full periphery thereof. In the illustrated embodiment, the flange 171 is sized to be received within the groove 164 of the distal housing member 126.

The body 170 of the septum 122 can define an upper or proximal face 172 and a lower or distal face 173. The upper and lower faces 172, 173 can also be referred to as surfaces. In the illustrated embodiment, the upper and lower faces 172, 173 face in opposite directions.

The septum 122 can further include a closure 174 that extends through a full thickness of the septum 122. In the illustrated embodiment, the closure 174 is formed as a slit 175 that extends through the full thickness of the septum 122. Stated otherwise, the closure 174 can extend fully between the upper and lower faces 172, 173. In the illustrated embodiment, the septum 122 is substantially oval shaped, or substantially ellipsoidal, and the slit 175 extends longitudinally along a major axis of the septum 122. The slit 175 may be formed in any suitable manner. In the illustrated embodiment, the slit 175 extends through the full thickness of the septum 122 substantially along a vertically oriented plane (in the orientation depicted in FIG. 12).

In the illustrated embodiment, the slit 175 is substantially defined by two opposing contact or sealing surfaces 176, 177. The sealing surfaces 176, 177 abut one another to close the closure 174. The sealing surfaces 176, 177 can be forced apart to transition the opening 174 to an open configuration in which fluid can pass through the closure 174. In some instances, a thickness T of septum 122 aids in ensuring that at least some portion of the sealing surfaces 176, 177 abut one another to maintain the closure 174 in a closed configuration, when desired. In various embodiments, the thickness T is no less than about 10, 11, 12, 13, 14, 15, 20, 30, or 40 thousandths of an inch; is no greater than about 15, 20, 30, or 40 thousandths of an inch; is within a range of from about 10 to about 15, 20, 30, or 40 thousandths of an inch; or is about 10, 11, 12, 13, 14, or 15 thousandths of an inch.

The septum 122 can be formed of any suitable elastomeric material, such as, e.g., silicone. The closure 174 can be biased toward the closed configuration. For example, in the illustrated embodiment, a pressure differential across the septum body 170 can exceed a threshold, or cracking pressure, at which the body 170 is elastically deformed from its natural or resting configuration to urge the sealing surfaces 176, 177 away from each other, thereby opening the closure 174. When the pressure differential drops below the threshold, the sealing surfaces 176, 177 can automatically come back into contact with each other as the body 170 returns to its natural state. As further discussed below, in the illustrated embodiment, the septum 122 exhibits a different cracking pressure in the ingress direction, as opposed to the egress direction, due to interactions between the septum 122 and the contact or restriction surfaces 146 of the fins 144. It is again noted that the cracking pressures correspond to differential pressures across the septum 122.

In some embodiments, a thickness of the septum body 170 is selected to ensure that the sealing surfaces 176, 177 will maintain the closure 174 in the closed configuration under a variety of circumstances that would otherwise lead to premature cracking of the slit 175, or stated otherwise, premature opening of the closure 174. For example, a relatively thicker septum 122 can accommodate minor variations in thickness across the septum body 170 that might arise from manufacturing anomalies to ensure that at least some portion of the sealing surfaces 176, 177 abut one another along the full length of the slit 175 to maintain the closure 174 in the closed orientation. In other or further instances, a relatively thicker septum 122 can accommodate minor deformations of the body 170 at both sides of the slit 174 that might arise from the long-term presence of a stylet or guidewire passing through the slit 174, such as when the valve 130 is prepackaged with a stylet passing therethrough.

In some embodiments, it can be desirable to have a relatively compliant septum body 170. For example, in some embodiments, the septum 122 is formed of a relatively soft silicone that can readily deform when a cracking pressure is reached. Further, in some instances, it may be relatively easier to control a thickness of the septum 122—e.g., to ensure that variations in the septum thickness are minimal or negligible from one septum 122 to the next during manufacture—than it may be to control the hardness of the septum material (e.g., silicone) from one septum to the next, or even from one lot of septum material to the next. Accordingly, employing relatively softer septum materials 122 can render the septum 122 less dependent on the softness or compliance of the septum 122 and more controlled by the physical geometry of the septum 122. This can lead to more predictable and repeatable cracking pressures. In various embodiments, the septum 122 is formed from a flexible silicone having a Shore A hardness of from about 30 to about 70, about 30 to about 60, about 30 to about 50, about 30 to about 45, about 35 to about 70, about 35 to about 60, about 35 to about 50, about 35 to about 45, about 40 to about 70, about 40 to about 50, about 40 to about 45, about 45 to about 70, about 45 to about 65, about 45, to about 60, about 45 to about 55, about 45 to about 50, or of about 30, 35, 40, 45, 50, 55, 60, 65, or 70.

In some embodiments, it can be advantageous to have a septum 122 that is both relatively thicker, for the reasons previously discussed, and relatively softer, for the reasons previously discussed. Further, in some instances, employing a relatively thicker septum 122 can accommodate relatively greater movement that may result from the material being more compliant.

In some instances, a relatively thinner septum 122 can be employed with a relatively smaller valve 110. For example, in some instances, a relatively smaller distance D between opposing faces of the support structures 144, as shown in FIG. 6, can permit use of a relatively thinner septum 122 in order to achieve the same aspiration cracking pressure of a valve having a larger distance D and a thicker septum 122 (of the same hardness). In some instances, a relatively smaller valve 110 can be desirable. Smaller valves 110 can, in some instances, reduce material costs and/or be less bulky or easier for a practitioner to manipulate.

In various embodiments, the distance D (FIG. 6) is no less than about 30, 35, 40, 45, 50, 55, or 60 thousandths of an inch; is no greater than about 30, 35, 40, 45, 50, 55, or 60 thousandths of an inch; is within a range of from about 30 to about 35, 40, 45, 50, 55, or 60 thousandths of an inch; is within a range of from about 35 to about 40, 45, 50, 55, or 60 thousandths of an inch; is within a range of from about 40 to about 45, 50, 55, or 60 thousandths of an inch; is within a range of from about 45 to about 50, 55, or 60 thousandths of an inch; or is about 35, 40, 45, 48, 50, 55, or 60 thousandths of an inch. In various embodiments, the distance D is no less than about 2, 3, 4, 5, or 6 times the thickness T (FIG. 12) of the septum 122, is no greater than about 2, 3, 4, 5, or 6 times the thickness T; is within a range of from about 2 to about 3, 4, 5, or 6 times the thickness T; is within a range of from about 3 to about 4, 5, or 6 times the thickness T; is within a range of from about 4 to about 5 or 6 times the thickness T; or is about 2, 3, 4, 5, or 6 times the thickness T. For example, in some embodiments, the thickness T is approximately 14 thousandths of an inch and the distance D is about 48 thousandths of an inch.

Figure 13:
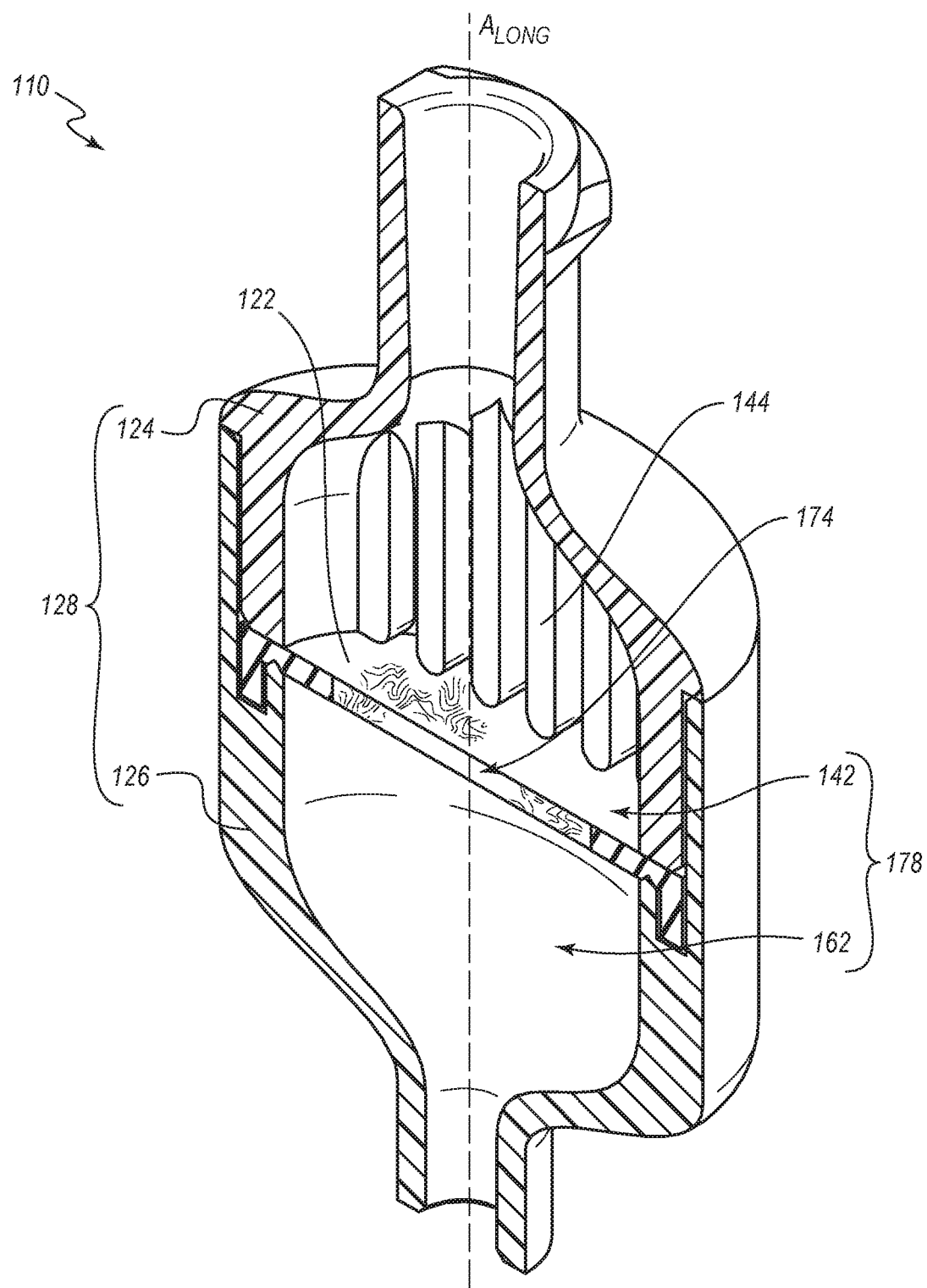
FIG. 13 is a cross-sectional perspective view of the valve of FIG. 2 taken along the view line 13-13 in FIG. 2.
Figure 14:
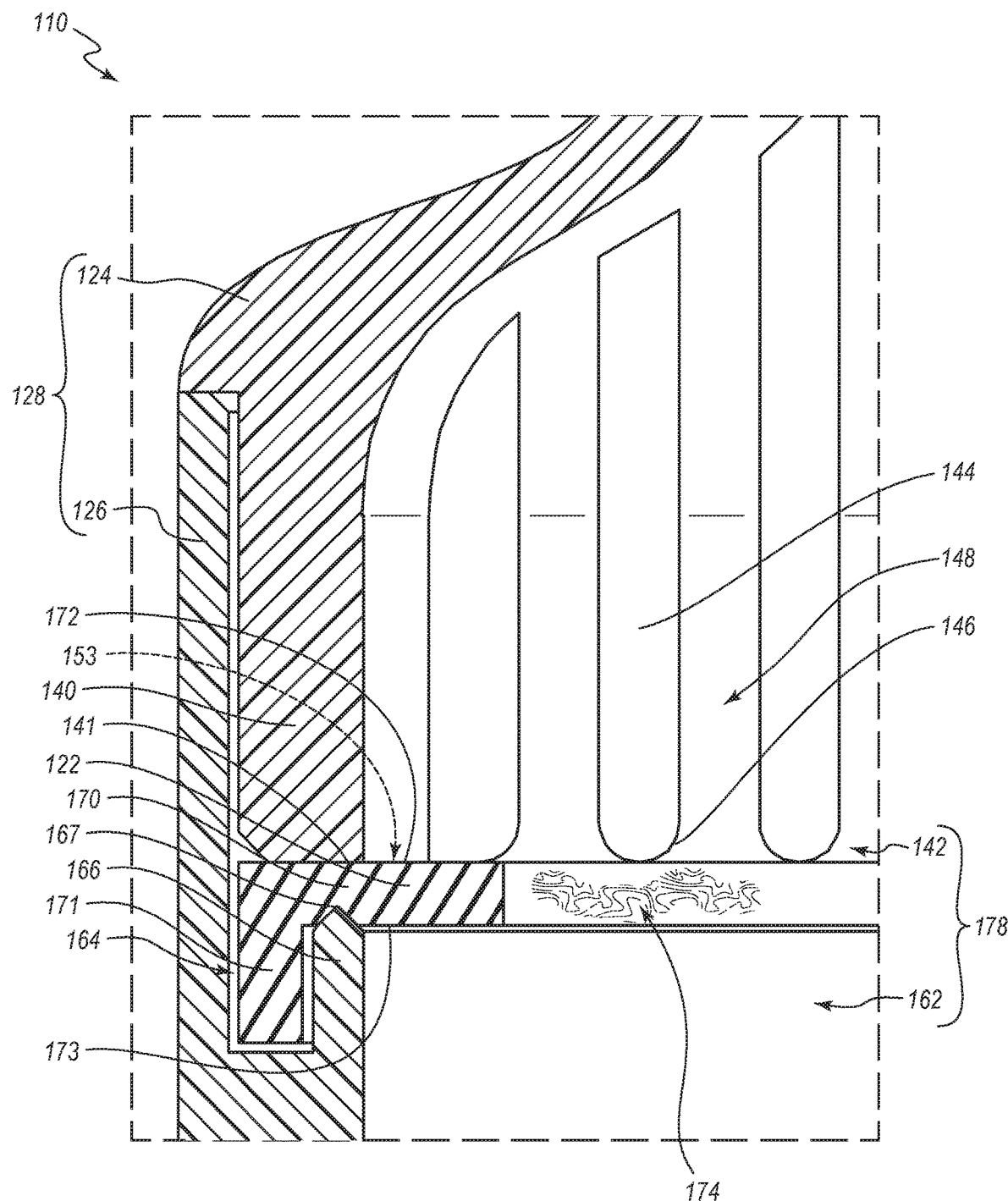
FIG. 14 is an enlarged cross-sectional view of a portion of the valve of FIG. 2.

FIGS. 13 and 14 depict cross-sectional views of the valve 110 in the assembled state. The proximal and distal housing members 124, 126 are joined together to form a housing 128 of the valve 110. The housing 128 includes a chamber 178 therein, which includes both the proximal and distal chambers 142, 162. The valve 110 defines a longitudinal axis $A_{LONG}$ that extends substantially vertically in FIG. 13, and is generally aligned with the direction of fluid flow through the valve 112 in each of the distal and proximal directions.

In the illustrated embodiment, the septum 122 is captured, trapped, or attached between the proximal housing member 124 and the distal housing member 126. The housing members 124, 126 can be formed of any suitable material, such as, e.g., any suitable polymeric material. In some embodiments, the polymeric material of at least the distal housing member 126 may be capable of forming a strong, fluid-tight bond with an extension leg 106, 107 (see FIG. 1). The housing members 124, 126 can be joined together in any suitable manner to ensure the septum 122 forms a fluid tight seal with each of the housing members 124, 126, in manners such as described below. For example, in various embodiments, the housing members 124, 126 are attached to each other via one or more of a friction fit, a snapping arrangement, one or more adhesives, solvent bonding, etc. For high-pressure applications, such as power injections, stronger attachment mechanisms, such as adhesives or solvent bonding, can be desirable.

In the illustrated embodiment, an active portion of the septum 122, as discussed further below, is positioned within the chamber 178, whereas immobilized portions along the periphery of the septum 122 are clamped between the housing members 124, 126 at positions external to the chamber 178. In many embodiments, only the active portion of the septum 122 is positioned within the chamber 178. It may be said that a portion (e.g., the active portion) of the septum 122 is positioned within the chamber 178.

The housing members 124, 126 can be secured together in a fixed longitudinal approximation in which the sealing rim 167 atop the septum support 166 compresses a thin portion of the septum 122 against the distal face 141 of the sidewall 140 of the proximal housing member 124. The gripped portion of the septum 122 can define a line (e.g., a line having a relatively small thickness) that extends about a full periphery of the septum body 170. Accordingly, in the illustrated embodiment, the gripped portion of the septum 122 can substantially define a continuous oval shape. The compression can be sufficiently great such that the proximal and distal housing members 124, 126 grip or tightly hold the septum 122 to prevent the entirety of the septum 122 from being pulled into either the proximal or distal chambers 142, 162 during use of the valve 110, or stated otherwise, can prevent the septum 122 from being disconnected from the housing, dislodged, ingested, or otherwise undesirably displaced into either the proximal or distal chambers 142, 162. Stated otherwise, advancement of the sealing rim 167 toward the distal face 141 of the sidewall 140 during assembly of the valve 110 can cause the sealing rim 167 to dig into or otherwise grip the septum 122, which can inhibit the septum 122 from being pulled inwardly (e.g., radially inward, or inward toward the longitudinal axis of the valve) under the influence of pressurized fluid. Any other suitable gripping features are contemplated, and may or may not be continuous about a full periphery or perimeter of the housing.

In the illustrated embodiment, the continuous gripping arrangement that fully and continuously extends about a periphery of the septum support 168 can form a first, or proximal, fluid-tight seal between the proximal housing member 124 and the proximal face 172 of the septum 122 that prevents fluid from escaping from the proximal chamber 142 thereat, and can form a second, or distal, fluid-tight seal between the distal housing member 126 and the distal face 173 of the septum 122 that prevents fluid from escaping from the distal chamber 162 thereat. The first and second seals can form along the gripped portion of the septum 122 about a full periphery of the septum body 170.

In the illustrated embodiment, the peripheral configuration of the septum 122 can further ensure that the septum 122 will not be entrained into, ingested, pushed or forced into, or otherwise undesirably displaced into the distal chamber 162 and potentially plug the valve 110 during infusion events. For example, it can be desirable to ensure that the septum 122 is not forced distally into the distal chamber 162 by high pressure fluid flow during power injections. In the illustrated embodiment, the septum flange 171 extends proximally into the groove 164, which can assist in maintaining the septum 122 in place. For example, in some instances when high pressure fluid is being passed distally through the valve, the flange 171 can grip the septum support 166 to prevent entrainment or ingestion of the septum 122.

With continued reference to FIGS. 13 and 14, in the illustrated embodiment, the fins 144 are arranged in two distinct groups that are positioned at opposite sides of the closure 174. Only one of the two sets is shown in FIG. 13; the other is shown, e.g., in FIGS. 4 and 6. In the illustrated embodiment, each set includes six fins 144. Other numbers of fins are contemplated. The fins 144 are arranged symmetrically relative to the closure. Moreover, in the illustrated embodiment, the two sets of fins 144 are mirror images of one another across a plane that passes through the closure 174, which corresponds to the plane of the cross-section in FIG. 13. In some instances, symmetrical arrangements can inhibit or prevent asymmetrical distortion of the closure 174, which can, in some instances, lead to unpredictability, variability, or non-repeatability of cracking pressures.

With continued reference to FIG. 14, the distal ends of the restriction surfaces 146 can contact or be in close proximity to the proximal face 172 of the septum 122 when the septum 122 is in a natural or relaxed state. Moreover, as previously discussed, in the illustrated embodiment, the restriction surfaces 146 are curved or rounded convexly, such that only a small portion thereof contacts the proximal face 172, whereas the vast majority of the restriction surfaces 146, as well as the remainder of the fins 144, is exposed to fluid within the proximal chamber 142. Thus, in certain embodiments, in circumstances in which there is substantially no pressure differential across the septum 122, a substantial majority of the restriction surfaces 146 can be exposed, or stated otherwise, can be separate from or not contact the septum 122. This can enable fluid to contact all or substantially all interior surfaces of the proximal housing member 124, when the proximal chamber 142 is filled with fluid. Stated otherwise, regions in which blood and/or microbes can become stagnant, stuck, and/or isolated from fluid flow can be reduced, minimized, or eliminated.

Moreover, during a flushing event, fluid (e.g., saline) is forced distally through the proximal housing member 124 at an elevated pressure. This pressure can cause the septum 122 to deform or bend away from the fins 144 in the distal direction, thereby exposing any portions of the restriction surfaces 146 that previously may have been in contact with the septum 122. Fluid is thus permitted to readily flow between the restriction surfaces 146 and the septum 122, thus flushing these regions.

For example, in some instances, a practitioner may couple a syringe or other device to the valve 110 to withdraw blood through the valve 110 in the proximal (e.g., aspiration) direction, such that blood may remain within the proximal chamber 142 at the end of the aspiration event. Thereafter, the practitioner may replace the syringe or other medical device with a separate medical device—e.g., a saline-filled syringe—to flush the valve 110, or more generally, to flush a full fluid path of the catheter assembly 100. The practitioner thus may depress the plunger of the syringe to pressurize the saline and force open the closure 174. As the pressurized saline is forced into and through the proximal chamber 142, the fins 144 direct the fluid to flow through the channels 148 and under the restriction surfaces 146, or stated otherwise, between the restriction surfaces 146 and the septum 122. Accordingly, the valve 110 reduces the amount of blood that could get trapped between the restriction surfaces 146 and the septum 122. Microbes and/or other undesirable materials may similarly be flushed from all or substantially all portions of the proximal chamber 142.

In the illustrated embodiment, the flushing channels 148 are oriented substantially longitudinally. That is, the flushing channels 148 extend in directions that are substantially parallel to the longitudinal axis $A_{LONG}$ of the valve 110 (see FIG. 13). Moreover, in the illustrated embodiment, the flushing channels 148 are defined, in part, by opposing faces of adjacent fins 144. In the illustrated embodiment, the opposing faces of adjacent fins 144 are substantially planar. In various embodiments, the planar opposing faces are substantially parallel to each other, and each smoothly transitions to the rounded distal ends. In some instances, such an arrangement of the flushing channels 148 can promote longitudinal fluid flow along the surface of the fins 144 and enhance flushing at the distal ends of the fins, such as to disrupt biofilm, clear out blood and/or microbes, etc. Other configurations of the fins 144 are contemplated.

The fins 144 can provide sufficient columnar strength in the longitudinal direction to resist any longitudinal deformation when the septum 122 is urged proximally during aspiration. For example, in some instances, longitudinal elongation of the fins 144 or ribs can enhance their longitudinal strength and support of the septum 122 as it is urged proximally.

Figure 15:
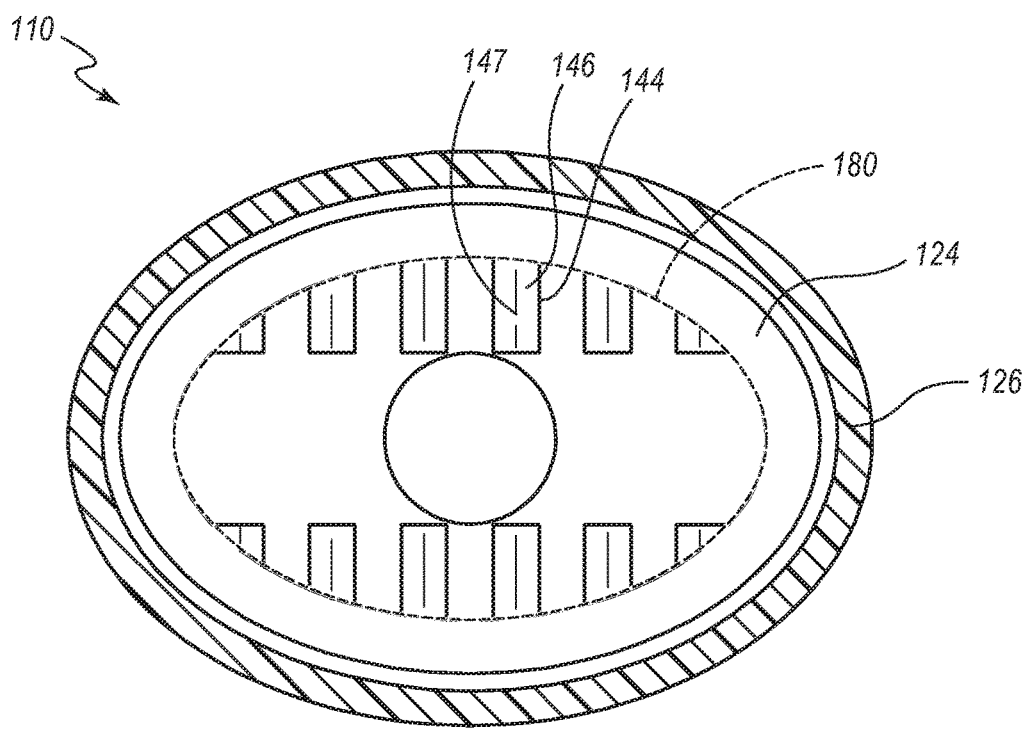
FIG. 15 is a cross-sectional view of the valve of FIG. 2 taken along the view line 15-15 in FIG. 2

FIG. 15 is a proximally directed cross-sectional view of the assembled valve 110, which depicts portions of the proximal housing member 124 and the distal housing member 126 at a position just above the septum. An oval-shaped sealing region inner limit 180, depicted in broken lines, identifies an inner edge of a region of pressure provided by the sealing rim 167 of the distal housing member 126 (see FIGS. 14 and 16). That is, as can be seen in FIG. 14, the sealing rim 167 presses the septum 122 against the distal face 141 of the sidewall 140 of the proximal housing member 124 to form the first and second (proximal and distal) seals, as previously discussed, and the sealing region inner limit 180 shown in FIG. 15 represents the inner limit of the proximal seal.

The portion of the septum 122 along which the proximal and distal seals are formed can correspond to an immobilized region of the septum 122. That is, the compressive grip provided by the proximal and distal housing members 124, 126 can provide seals between the housing members 124, 126 and the septum 122 and can also substantially fix a thin region of the septum 122 along a fully periphery of the septum 122. This sealing and immobilization region can demarcate an outer edge of an active region 182 of the septum 122 (see FIG. 17), or stated otherwise, can serve as a fixed outer boundary 184 to a portion of the septum 122 that is permitted to move in at least one direction (i.e., distally and, in some areas, proximally as well).

Figure 16:
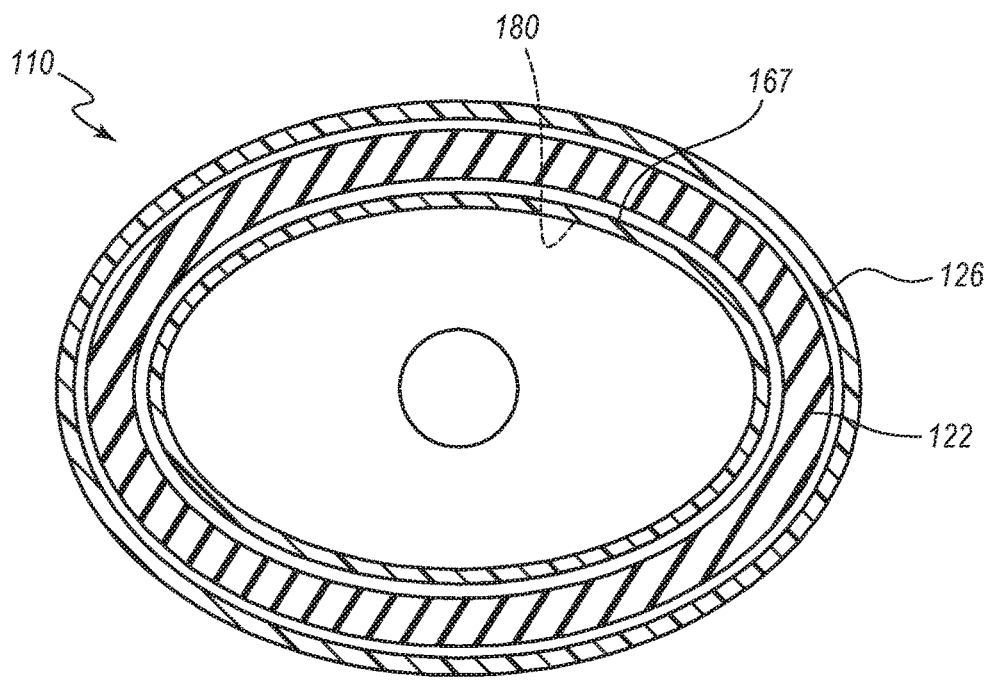
FIG. 16 is a cross-sectional view of the valve of FIG. 2 taken along the view line 16-16 in FIG. 2.

Stated in yet another manner, the sealing region inner limit 180 previously identified can have an identical or substantially identical footprint to that of the sealing rim 167—for example, an inner periphery of the sealing region inner limit 180 may correspond to an inner edge of the sealing rim 167 (see FIG. 16). This inner periphery of the sealing region can correspond to an outer perimeter 184 of the active region 182 of the septum body 170 (see FIG. 17), as discussed further below. Note that the septum 122 is not shown in either FIG. 15 or 16, but is instead shown and discussed with respect to FIG. 17.

In FIG. 15, the distal ends of the fins 144 are also shown. As previously discussed, these distal ends correspond to the restriction surfaces 146, which interact with the septum 122 to inhibit, restrict, delimit, or prevent proximal movement of specific regions of the septum 122. As previously mentioned, in many instances, only a small portion of the restriction surfaces 146 (e.g., the linear regions 147, which are oriented vertically in the present view) interact with—e.g., contact to resist or oppose proximal movement of—the septum 122. In some instances, the septum 122 may contact greater portions of the restriction surfaces 146 due to pressure-induced deformation during aspiration.

With reference to FIG. 16, the inner edge of the rim 167 of the distal housing member 126 is shown. As previously discussed the illustrated embodiment, this inner edge can correspond to the sealing region inner limit 180 and the outer peripheral limit or outer perimeter 184 of the active region 182 of the septum body 170 (see FIG. 17).

Figure 17:
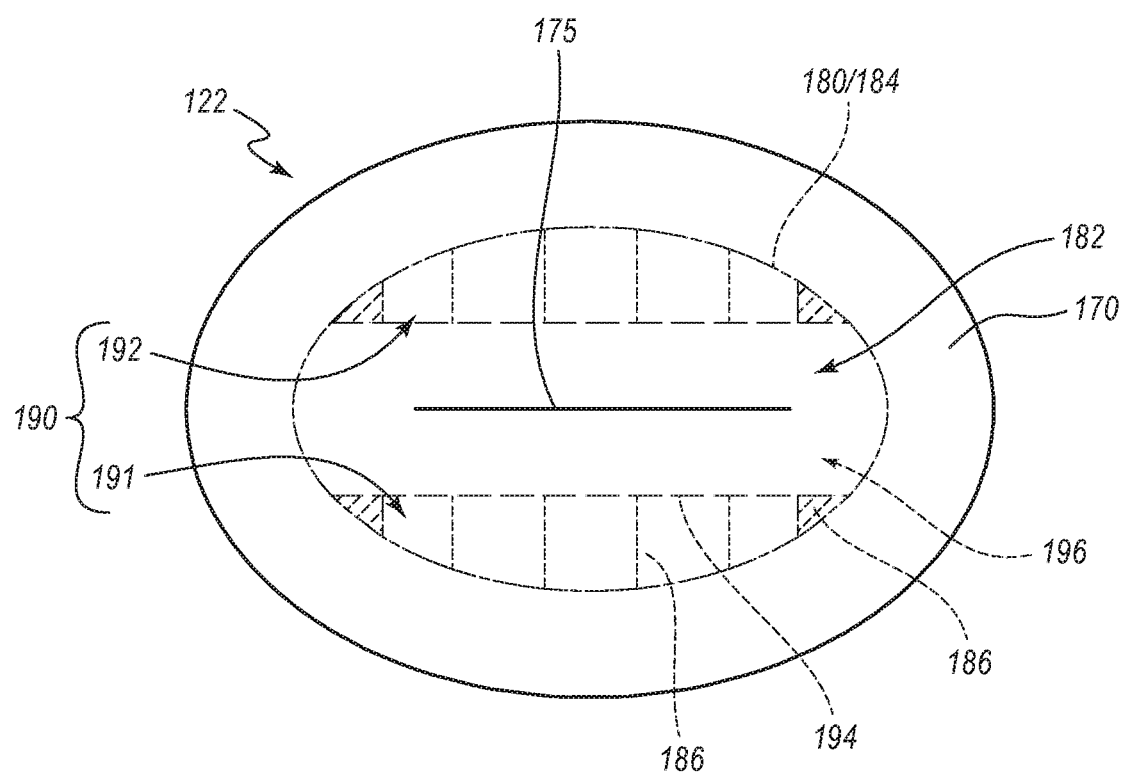
FIG. 17 is a top plan view of the septum with an active portion of the septum shown in a first style of broken lines, with contact portions of the septum shown in a second style of broken lines, and with the inner boundaries of resultant restricted regions of the septum shown in a third style of broken lines.

FIG. 17 is a top plan view of the septum 122, with the outer perimeter 184 of the active region 182 shown as a broken line. As previously mentioned, the outer perimeter 184 of the active region 182 can correspond to the inner edges of the sealing regions that result from clamping the septum 122 between the proximal and distal housing members 124, 126. The outer perimeter 184 of the active region 182 is shown in a first style of broken lines.

FIG. 17 also depicts contact regions 186 at which the septum 122 contacts the restriction surfaces 146 of the fins 144. The contact regions 186 are shown in a second style of broken lines. Most of the contact regions 186 are substantially rectilinear and are oriented orthogonally relative to a major axis of the septum 122, which major axis is aligned with the slit 175 in the illustrated embodiment. Four substantially triangular contact regions 186 are also present: one at each end of the two rows of substantially rectilinear contact regions 186.

The contact regions 186 can define a restricted portion 190 of the active region 182 of the septum 122. The restricted portion 190 represents one or more regions of the septum 122 that are inhibited from moving proximally. In the illustrated embodiment, this inhibition is provided by the restriction surfaces 146 of the fins 144. Further, in the illustrated embodiment, the restricted portion 190 includes two separate, distinct restricted regions 191, 192 at opposite sides of the septum 122. The inner edges of the restricted regions 191, 192 are shown in a third style of broken lines. In the illustrated embodiment, these inner edges are aligned with the longitudinal planes 150, 151 discussed previously (see FIG. 6).

As can be seen in FIG. 17, the outer perimeter 184 of the active region 182 can substantially correspond with an inner perimeter defined by the sidewall 160, and in particular, an inner perimeter defined by the septum support 166 portion of the sidewall 160. In the illustrated embodiment, the outer perimeter 184 is substantially oval. The outer perimeter 184 may be said to define a continuously curved shape. The active region 182 can further include an inner perimeter 194 that is at least partially defined (i.e., at its rounded ends) by the septum support 166, and is otherwise bounded by the restricted regions 191, 192. In the illustrated embodiment, the restricted regions 191, 192 provide substantially rectilinear boundaries to the inner perimeter 194. The inner perimeter 194 is thus substantially shaped as a stadium in the illustrated embodiment, with rectilinear sides and rounded opposing ends. The portion of the active region 182 that is interior to the inner perimeter 194 may be termed as a secondary active region 196. The full active region 182 may also be referred to as the primary active region 182.

In certain embodiments, the septum 122 can bend or pivot along the various boundaries just described—specifically, the outer perimeter 184 and the inner perimeter 194. For example, in some embodiments, during an infusion event, distal movement of the full active region 182 can be unopposed, and the septum 122 may thus bend or pivot distally along the outer perimeter 184. Similarly, during an aspiration event, proximal movement of the restricted regions 191, 192 can be opposed by the fins 144, such that only the secondary active region 196 may move unopposed in the proximal direction. In such instances, the septum 122 may bend or pivot proximally along the inner perimeter 194.

In use, an entirety of the active region 182 is capable of moving in the distal direction unopposed by any portion of the fins 144. That is, both the secondary active region 196 and the restricted regions 191, 192 of the septum 122 can move distally without any opposition from the fins 144. However, the restricted regions 191, 192 of the septum 122 are inhibited from proximal movement by the fins 144 in manners such as previously discussed. As a result, a greater portion of the septum 122 is permitted to move in the proximal direction or stated otherwise, fluid pressure can act, unopposed, on a greater portion of the septum 122. Accordingly, the slit 175 can open at a lower pressure differential, or cracking pressure, in the distal or ingress direction than it does in the proximal or egress direction. Stated otherwise, during infusion, the full, oval-shaped primary active region 182 of the septum 122 can be acted on and urged distally such that a lower cracking pressure of the slit 175 can be achieved, as compared with an aspiration event, in which only the stadium-shaped, smaller, secondary active region 196 can be acted on unopposed by the fins 144 such that the slit 175 is more difficult to open in the proximal direction and such that a higher cracking pressure of the slit 175 is exhibited. Stated in yet another way, the fins 144 permit free movement of the septum 122, including the restricted portion 190 of the septum 122, in the distal or ingress direction; and oppose or inhibit movement of the septum 122, and in particular the restricted portion 190 of the septum 122, in the proximal or egress direction, thus resulting in a higher cracking pressure of the septum in the proximal or egress direction.

In various embodiments, an area of the primary active region 182 is no less than about 1.25, 1.5, 1.75, 2, 2.5, or 3; is no more than about 1.25, 1.5, 1.75, 2, 2.5, or 3; or is within a range of from about 1.25 to about 1.5, 1.75, 2, 2.5, or 3; from about 1.5 to about 1.75, 2, 2.5, or 3; from about 1.75 to about 2, 2.5, or 3; from about 2 to about 2.5 or 3; or from about 2.5 to about 3 times greater than an area of the secondary active region 196.

In various embodiments, the cracking pressure in the proximal direction is no less than 3, 4, 5, 6, 7, 8, 9, 10, 11, 12, 13, 14, or 15 times; no greater than 3, 4, 5, 6, 7, 8, 9, 10, 11, 12, 13, 14, or 15 times; within a range of from 3 to 5, 3 to 8, 3 to 10, 3 to 15, 5 to 8, 5 to 10, 5 to 15, 8 to 10, 8 to 15, or 10 to 15 times; or is about 3, 4, 5, 6, 7, 8, 9, 10, 11, 12, 13, 14, or 15 times the cracking pressure in the distal direction. In some embodiments, the cracking pressure in the distal direction, or the infusion cracking pressure, is no less than about 0.1, 0.15, 0.2, 0.25, 0.3, 0.35, 0.4, 0.5, 0.75, 1.0, 1.25, 1.5, 1.75, or 2.0 psig; is no greater than about 0.1, 0.15, 0.2, 0.25, 0.3, 0.35, 0.4, 0.5, 0.75, 1.0, 1.25, 1.5, 1.75, or 2.0 psig; is within a range of from about 0.1, 0.15, 0.2, 0.25, 0.3, 0.35, 0.4, 0.5, 0.75, 1.0, 1.25, 1.5, or 1.75 to about 2.0 psig; is within a range of from about 0.1, 0.15, 0.2, 0.25, 0.3, 0.35, 0.4, 0.5, 0.75, 1.0, 1.25, or 1.5 to about 1.75 psig; is within a range of from about 0.1, 0.15, 0.2, 0.25, 0.3, 0.35, 0.4, 0.5, 0.75, 1.0, or 1.25 to about 1.5 psig; is within a range of from about 0.1, 0.15, 0.2, 0.25, 0.3, 0.35, 0.4, 0.5, 0.75, or 1.0 to about 1.25 psig; is within a range of from about 0.1, 0.15, 0.2, 0.25, 0.3, 0.35, 0.4, 0.5, or 0.75, to about 1.0 psig; or is about 0.1, 0.15, 0.2, 0.25, 0.3, 0.35, 0.4, 0.5, 0.75, 1.0, 1.25, 1.5, 1.75, or 2.0 psig. In these or in further embodiments, the cracking pressure in the proximal direction, or the aspiration cracking pressure, is no less than about 1.0, 1.5, 2.0, 2.5, 3, 4, 5, 6, 7, 8, 9, or 10 psig; is no greater than about 1.0, 1.5, 2.0, 2.5, 3, 4, 5, 6, 7, 8, 9, or 10 psig; is within a range of from about 1.0, 1.5, 2.0, 2.5, 3, 4, 5, 6, 7, 8, or 9 to about 10 psig; is within a range of from about 1.0, 1.5, 2.0, 2.5, 3, 4, 5, 6, 7, or 8 to about 9 psig; is within a range of from about 1.0, 1.5, 2.0, 2.5, 3, 4, 5, 6 or 7 to about 8 psig; is within a range of from about 1.0, 1.5, 2.0, 2.5, 3, or 4 to about 5 psig; or is about 1.0, 1.5, 2.0, 2.5, 3, 4, 5, 6, 7, 8, 9, or 10 psig. In various embodiments, precise cracking pressures are achievable from one valve to the next, or stated otherwise, the valves can be produced with tight tolerances. In various embodiments, each of the distal and proximal cracking pressures for a manufacturing lot of valves can fall within a tolerance range of no more than ±0.1 psi or ±0.2 psi. In further instances, the same tolerances are possible from one manufacturing lot to the next, even when different lots of septum materials are used. Stated otherwise, the cracking pressures can be relatively unaffected by minor differences material hardness from one lot of manufacturing materials to the next. In various embodiments, the foregoing cracking pressures can be achieved in embodiments of valves for which the septum 122 satisfies the hardness conditions previously described and/or that meets the septum thickness T and/or the support structure separation distance D criteria previous described.

As previously discussed, in some instances, it can be advantageous for only a small portion of the restriction surfaces 146 to come into contact with the septum 122, as this can reduce the area in which blood or pathogens could become trapped between the proximal housing member 124 and the septum 122. Thus, it can be advantageous for the contact regions 186 of the septum 122 to represent only a small portion of the total area of the restricted portion 190 of the septum 122 that is effectively inhibited from proximal movement by the fins 144. In various embodiments, a collective total area of the contact regions 186 of the septum 122 is no greater than 10, 20, 30, 40, or 50 percent of the area of the restricted portion 190.

FIGS. 18-30 depict another embodiment of a bidirectional valve 210 that can resemble embodiments of the valve 110 previously discussed in certain respects. Accordingly, like features are designated with like reference numerals, with the leading digits incremented to "2." Relevant disclosure set forth above regarding similarly identified features thus may not be repeated hereafter. Moreover, specific features of the valve 210 that correspond to features of the valve 110 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 210 and components thereof. Any suitable combination of the features and variations of the same described with respect to the valve 110 can be employed with the valve 210, and vice versa. This pattern of disclosure applies equally to further embodiments depicted in subsequent figures and described hereafter, wherein the leading digits may be further incremented.

Figure 18:
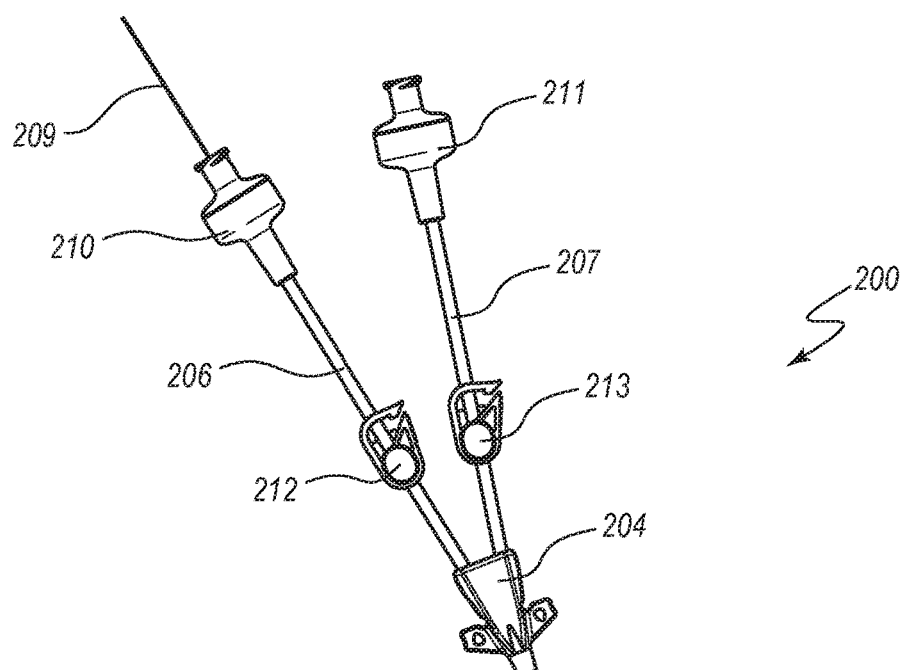
FIG. 18 is a perspective view of another embodiment of a dual lumen PICC that includes a pair of medical valves, each valve being in fluid communication with a separate lumen of a catheter shaft, and each valve being another embodiment of a bidirectional medical valve that permits fluid flow through the valve in either an infusion direction or an aspiration direction.

With reference to FIG. 18, the valve 210 is shown incorporated into a catheter assembly 200, which can include an additional valve 211. The catheter assembly 200 can resemble the catheter assembly 100 in many respects, and can include a catheter shaft 202, a junction 204, a pair of extension legs 206, 207, and a pair of clamps 212, 213. In the illustrated embodiment, the catheter assembly 200 further includes a stylet 209 that extends through the valve 210, the extension leg 206, the junction 204, and a lumen defined by the catheter shaft 202. In some embodiments, the stylet 209 is prepackaged with the catheter assembly 200 in the depicted orientation. In other embodiments, a user may insert the stylet 209 as shown prior to using the assembly 200. Use of the stylet for insertion and/or positioning of the catheter shaft 202 within the vasculature of the patient can proceed in any suitable manner, including those known in the art. In other embodiments, the stylet 209 may be omitted.

Figure 19:
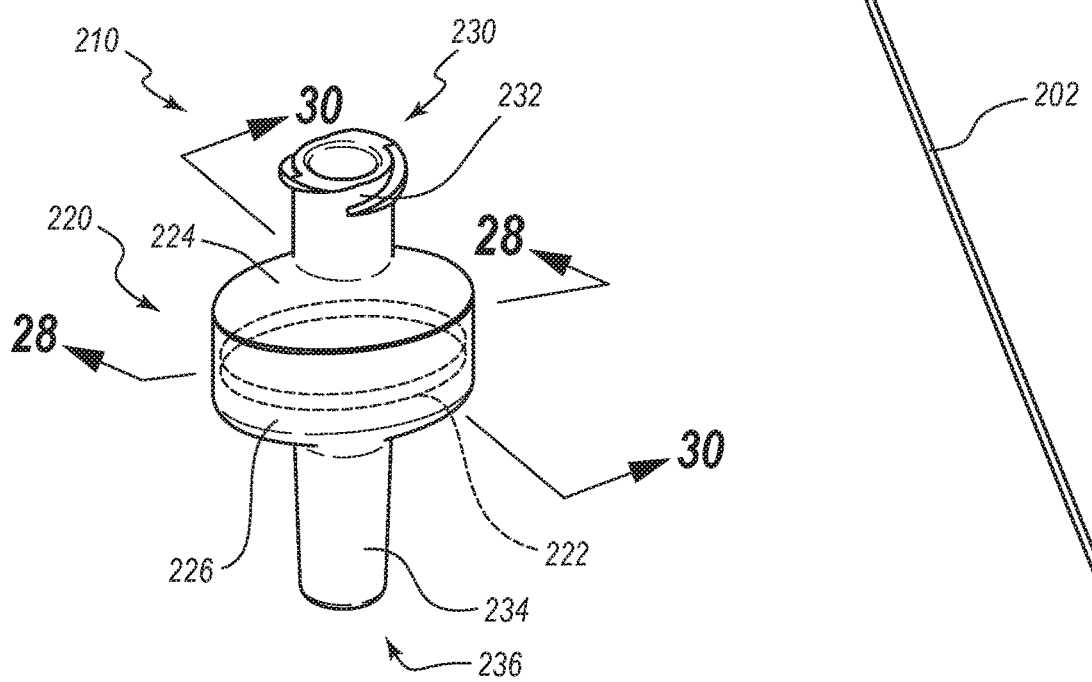
FIG. 19 is a perspective view of an embodiment of a bidirectional medical valve, such as either of the valves depicted in FIG. 18.
Figure 20:
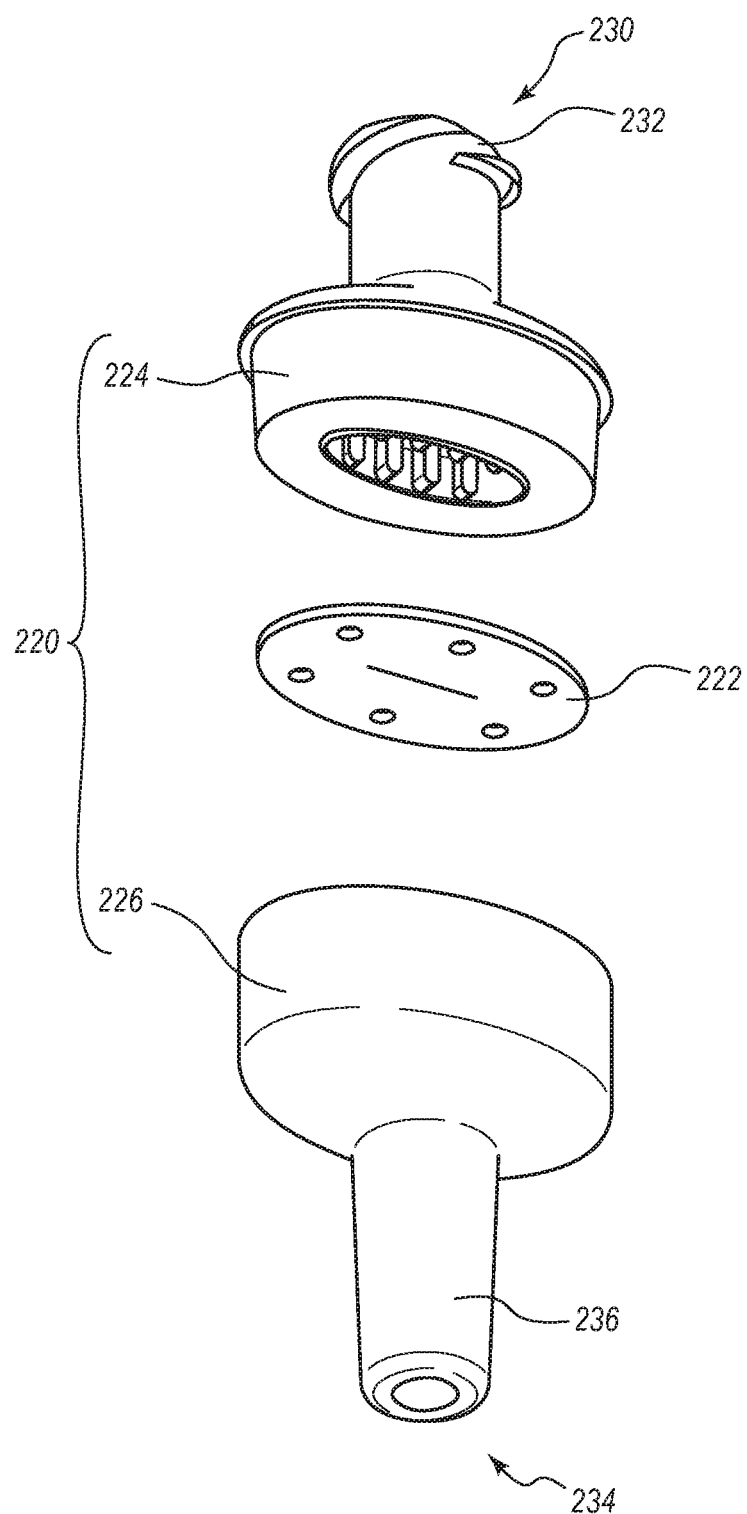
FIG. 20 is an exploded perspective view of the valve of FIG. 19.

With reference to FIGS. 19 and 20, the valve 210 can include a housing 220 and a septum 222. The housing 220 may include proximal and distal housing members 224, 226 that are fixedly secured to each other in any suitable manner. The housing members 224, 226 can be fixedly secured to the septum 222, as discussed further below.

The proximal housing member 224 can include a connection interface 230 that is configured to couple with one or more medical devices for infusion through the valve 210 in the ingress direction or for aspiration through the valve 210 in the egress direction. In the illustrated embodiment, the connection interface 230 comprises a Luer fitting 232. The distal housing member 226 can similarly include a connection interface 234. In the illustrated embodiment, the connection interface 234 comprises a protrusion or port 236 that is configured to be fixedly secured to a proximal end of an extension tube in any suitable manner, and generally in a fluid-tight manner. For example, in some embodiments, the distal housing member 226 can be overmolded onto an extension leg 206, 207. Other forms of attachment are also contemplated.

Figure 21:
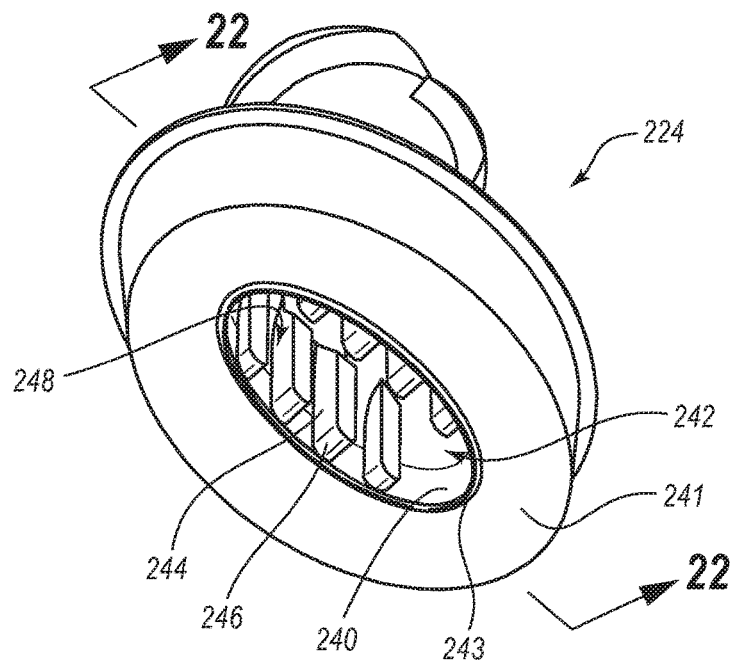
FIG. 21 is a bottom perspective view of an embodiment of a first housing piece of the valve of FIG. 19.
Figure 22:
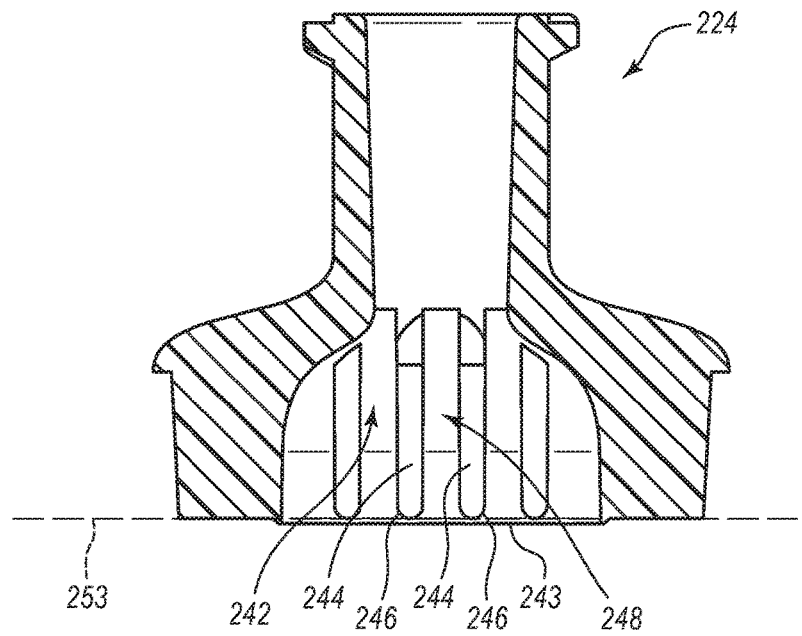
FIG. 22 is a cross-sectional view of the first housing piece taken along the view line 22-22 in FIG. 21.
Figure 23:
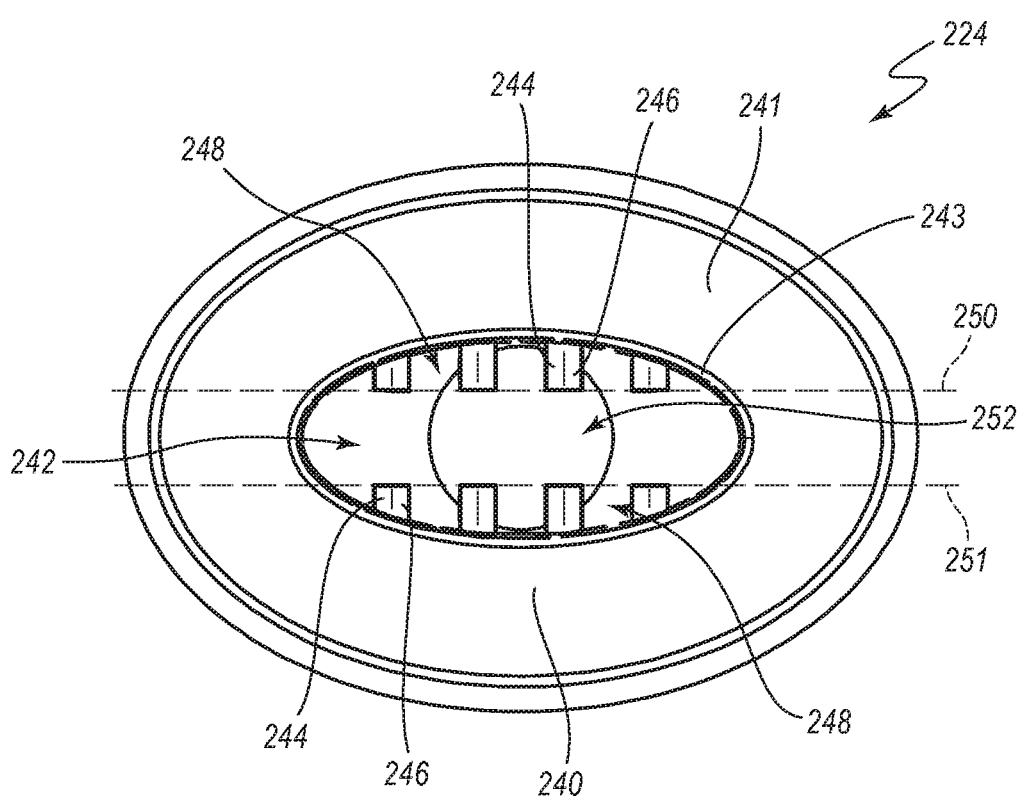
FIG. 23 is a bottom plan view of the first housing piece.

With reference to FIGS. 21-23, the proximal housing member 224 can include a sidewall 240 that defines a proximal chamber 242. The sidewall 240 can terminate at a distal face 241. In the illustrated embodiment, a sealing rim or gripping rim 243 is positioned at an interior edge of the sidewall 240 and extends distally relative to the sidewall 240. As discussed below, the gripping rim 243 can cooperate with the septum 222 to generate proximal and distal seals and can assist in gripping the septum 222 to inhibit or prevent ingestion of the septum 222 in manners similar to those discussed above with respect to the sealing or gripping rim 167.

The proximal housing member 224 can further include a plurality of support structures 244 that extend inwardly away from the sidewall 240 into the proximal chamber 242. Each fin 244 defines a contact or restriction surface 246 at a distal end thereof. Moreover, each pair or adjacent fins 244 defines a fluid channel 248 therebetween. The illustrated embodiment includes eight total fins 244, which are arranged in two symmetrical groups of four fins 244 mirrored across a longitudinal plane through the proximal housing member 224 (i.e., the plane of the cross-section of FIG. 22).

With reference to FIG. 22, in the illustrated embodiment, each restriction surface 246 extends to and touches a lateral plane 253. The gripping rim 243 projects distally past this plane 243.

Figure 28:
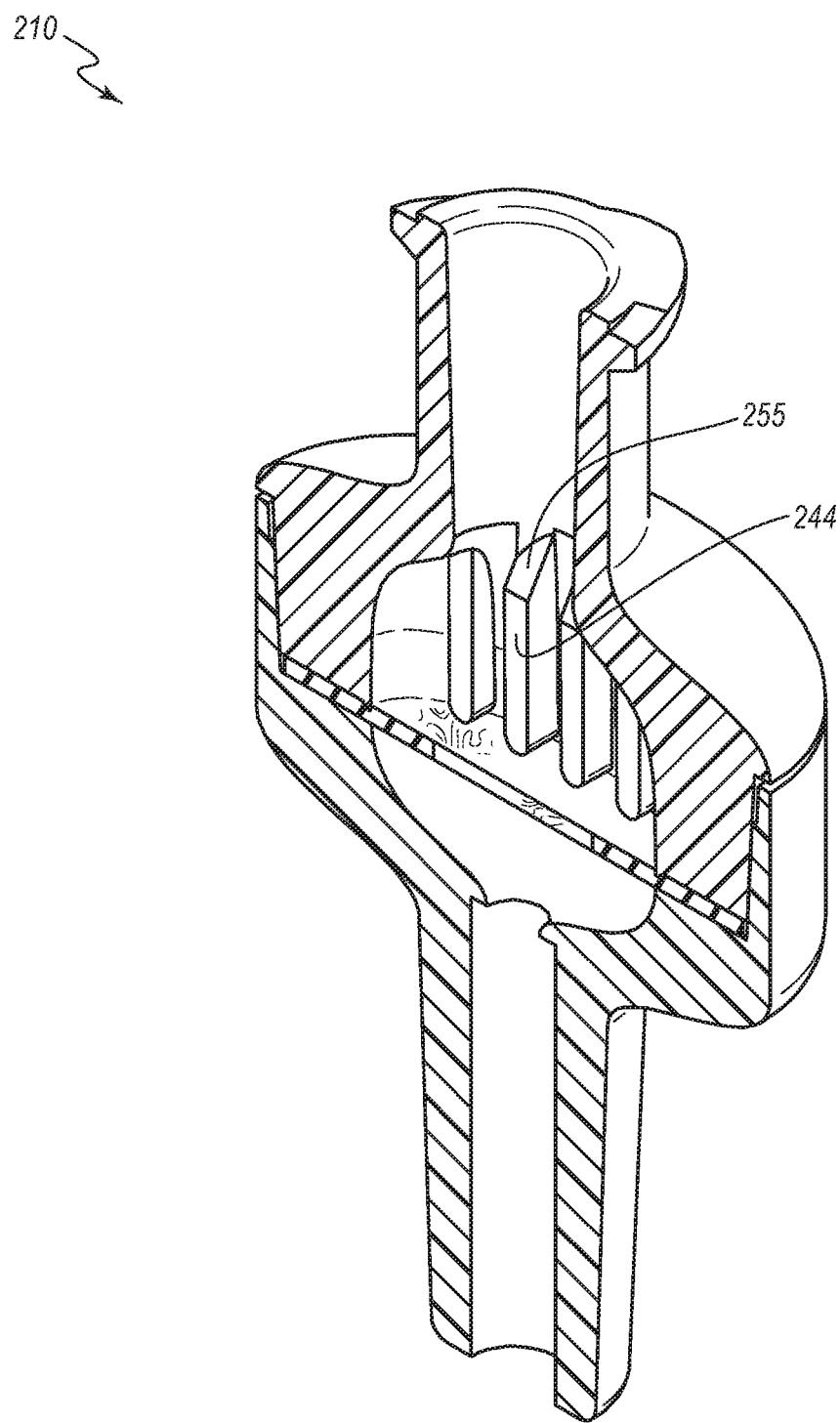
FIG. 28 is a cross-sectional perspective view of the valve of FIG. 19 taken along the view line 28-28 in FIG. 19.

With reference to FIG. 23, in the illustrated embodiment, each restriction surface 246 extends inwardly from the sidewall 240 and terminates at one of two longitudinal planes 250, 251. The fins 244 likewise each terminate at an interior end thereof at a planner surface, which is coplanar with one of two longitudinal planes 250, 251. In the illustrated embodiment, the planes 250, 251 each extend through a proximal opening 252. This arrangement can be relatively more compact than the more spaced-apart arrangement of the proximal housing member 124 depicted in FIG. 6. In such a compact arrangement, the fins 244 extend into a flow path of fluid that enters into the valve 210 through the proximal opening 252. In some embodiments, as shown in FIG. 28, angled surfaces or ramps 255 can be positioned at upper ends of one or more of the fins 244 to reduce or avoid disruption of the fluid flow, such as the formation of turbulence, eddies, etc.

Figure 24:
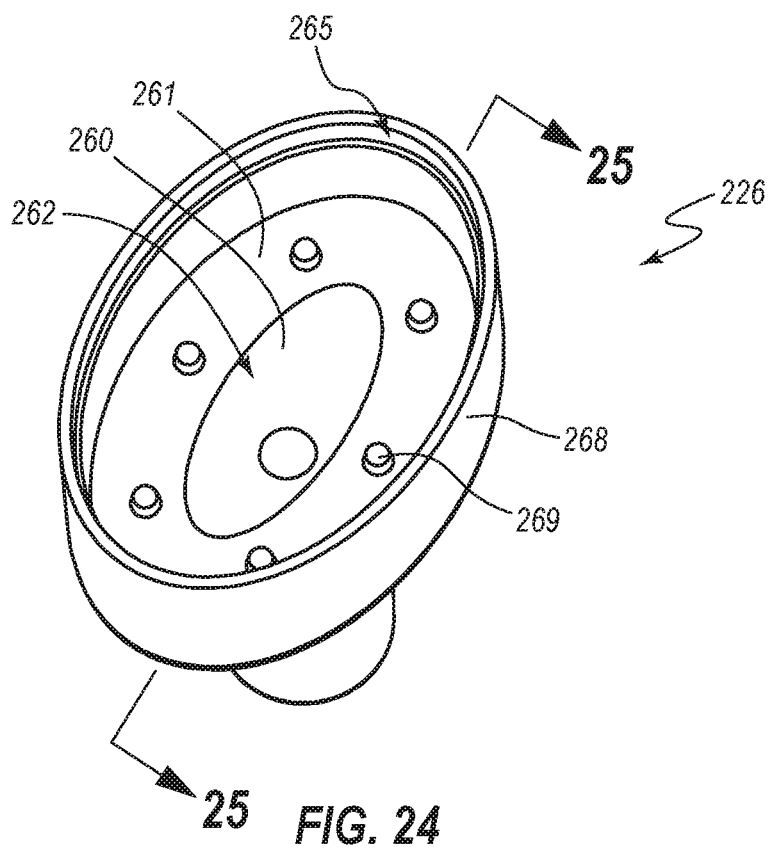
FIG. 24 is a top perspective view of an embodiment of a second housing piece of the valve of FIG. 19.
Figure 25:
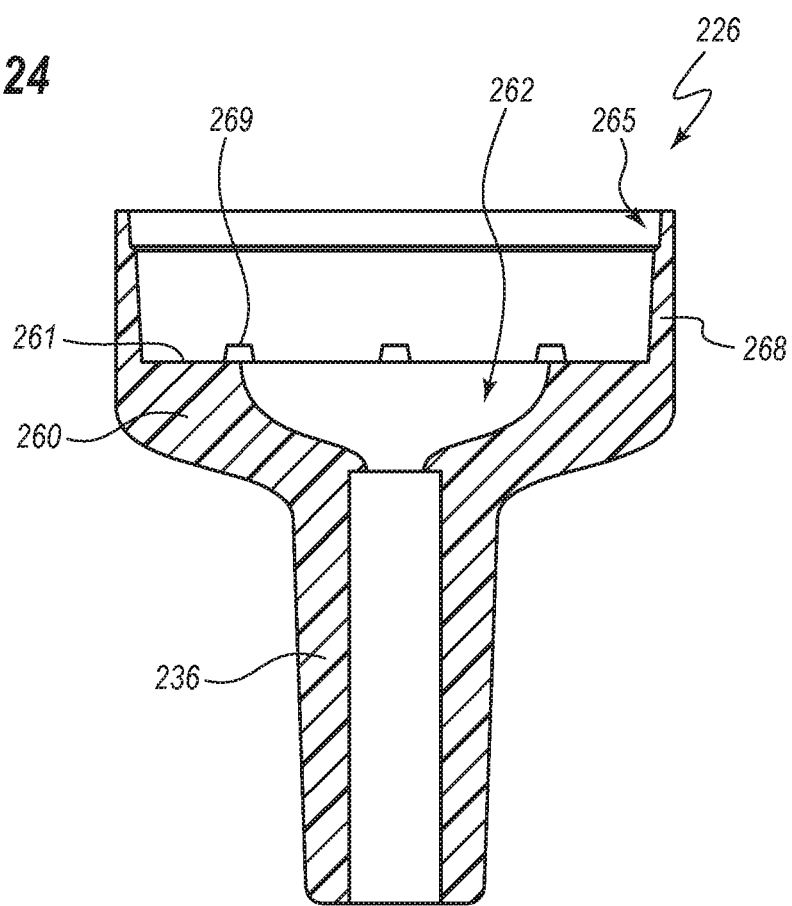
FIG. 25 is a cross-sectional view of the second housing piece taken along the view line 25-25 in FIG. 24.

With reference to FIGS. 24 and 25, the distal housing member 226 includes a sidewall 260 that defines a distal chamber 262. In the illustrated embodiment, the distal housing member 226 further includes a plurality of retention members, anchors, or posts 269 that extend proximally from a proximal surface 261 of the sidewall 260. The illustrated embodiment includes six posts 269. In the illustrated embodiment, the posts 269 are shaped substantially as frustocones, although other shapes and configurations are contemplated (e.g., cylindrical). In some instances, the frustoconical shape can assist in an assembly process, as the shape can facilitate placement of the septum 222 onto the posts, as further discussed below. In the illustrated embodiment, the posts 269 are regularly spaced about a full periphery of the distal chamber 262.

In some embodiments, the distal housing member 226 includes an outer sleeve 268 that can be positioned over and coupled with the proximal housing member 224. Any suitable attachment mechanism is contemplated, and is desirably fluid tight. In some embodiments, the outer sleeve 268 can be adhered or solvent bonded to the proximal housing member 224, and in further embodiments, the connection thus achieved can be fluid-tight, even at elevated pressures associated with power injections.

Figure 29:
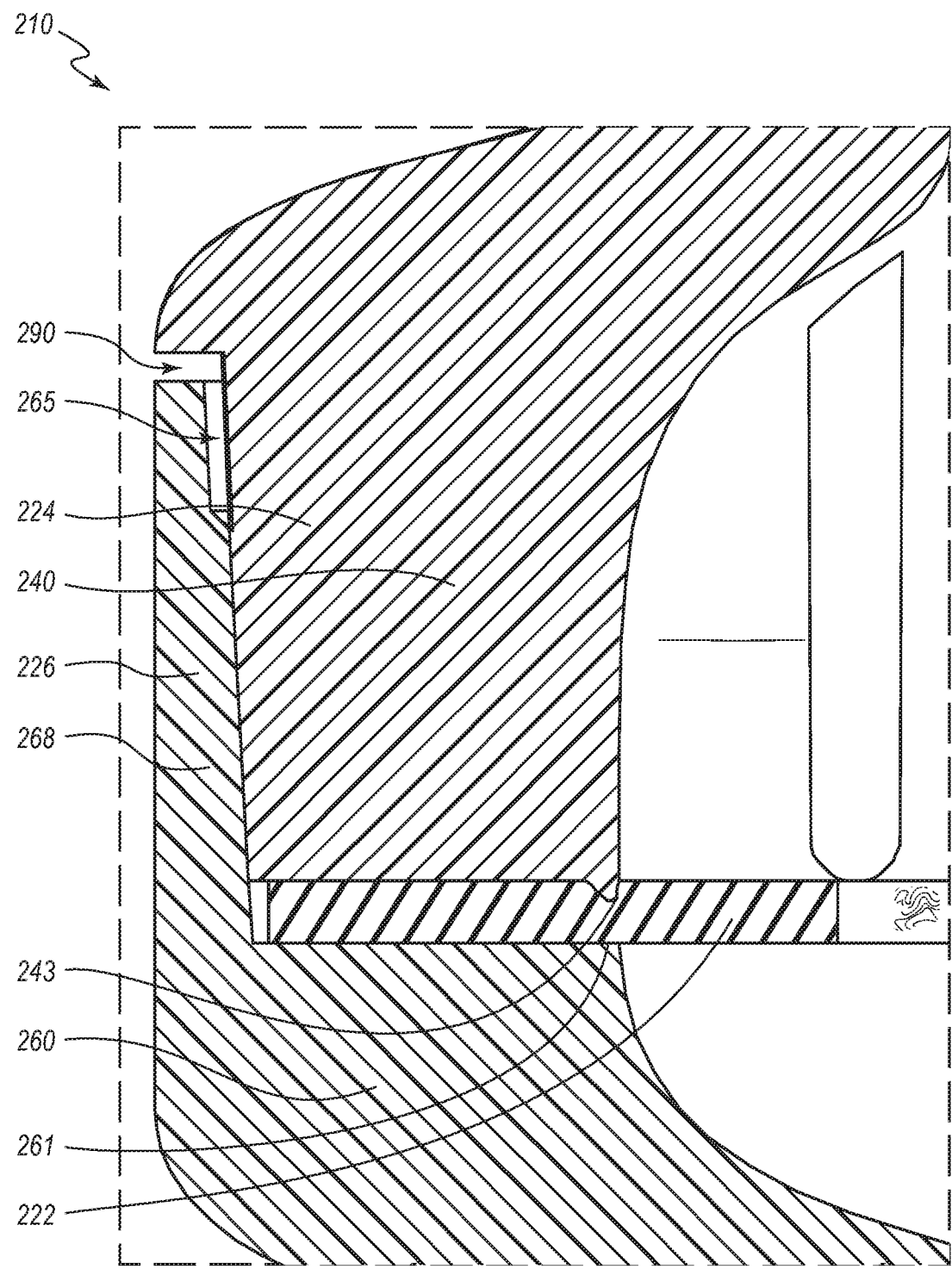
FIG. 29 is an enlarged cross-sectional view of a portion of the valve of FIG. 19.

In some embodiments, the outer sleeve 268 includes a groove 265 which, in cooperation with the proximal housing member 224, can define a port or solvent vent 290, as shown in FIG. 29. In the illustrated embodiment, the groove 265 and the solvent vent 290 extend about a full periphery of the assembled valve 210. During manufacture of the valve 210, an appropriate solvent can be provided to an outer surface of the sidewall 240 of the proximal housing member 224 and/or an inner surface of the outer sleeve 268 of the distal housing member 264. As the housing members 224, 264 are subsequently advanced together, liquified portions of these members may be forced into at least a portion of the vent 290. In other or further instances, once the housing members 224, 264 are fully coupled together, the vent 290 may provide an egress port the which the solvent can evaporate. In the illustrated embodiment, the distal housing member 226 defines the groove 265. In other embodiments, the proximal housing member 224 may additionally or alternatively define the groove.

With reference again to FIG. 25, in certain embodiments, the protrusion 236 can be attached to the proximal end of an extension leg in any suitable manner, as previously mentioned. In some instances, the protrusion 236 defines a lumen that receives the extension leg, and an opening at the proximal end of the lumen can, in some instances, be sized to be substantially identical to an inner diameter of the extension leg.

Figure 26:
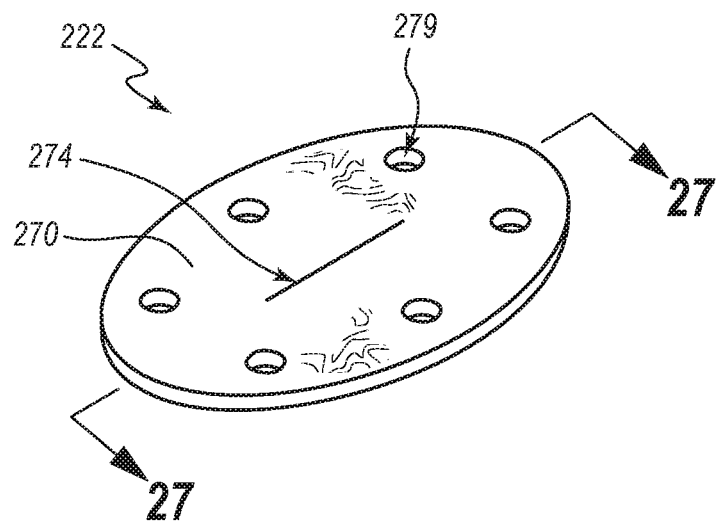
FIG. 26 is an upper perspective view of an embodiment of a septum of the valve of FIG. 19.
Figure 27:
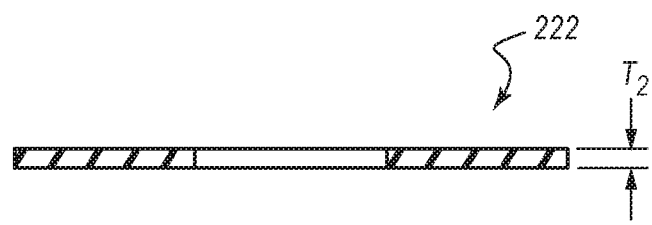
FIG. 27 is a cross-sectional view of the septum taken along the view line 27-27 in FIG. 26.

FIGS. 26 and 27 depict an embodiment of the septum 222, which includes a main septum body 270 and a closure 274. In the illustrated embodiment, the septum 222 further includes a plurality of openings, apertures, or channels 279 that fully extend through the body 270. The channels 279 can extend about a periphery of the septum 222. In the illustrated embodiment, the septum 222 includes six channels that are regularly spaced around a periphery thereof. Other arrangements and orientations are contemplated.

The channels 279 can be formed in any suitable manner. In some embodiments, the channels 279 are cut or stamped from the body 270. In other embodiments, the septum 222 is molded to include the channels 279.

In the illustrated embodiment, the septum 222 defines a uniform thickness $T_2$. The septum 222 is devoid of peripheral flanges, such as discussed above with respect to the septum 122.

Figure 30:
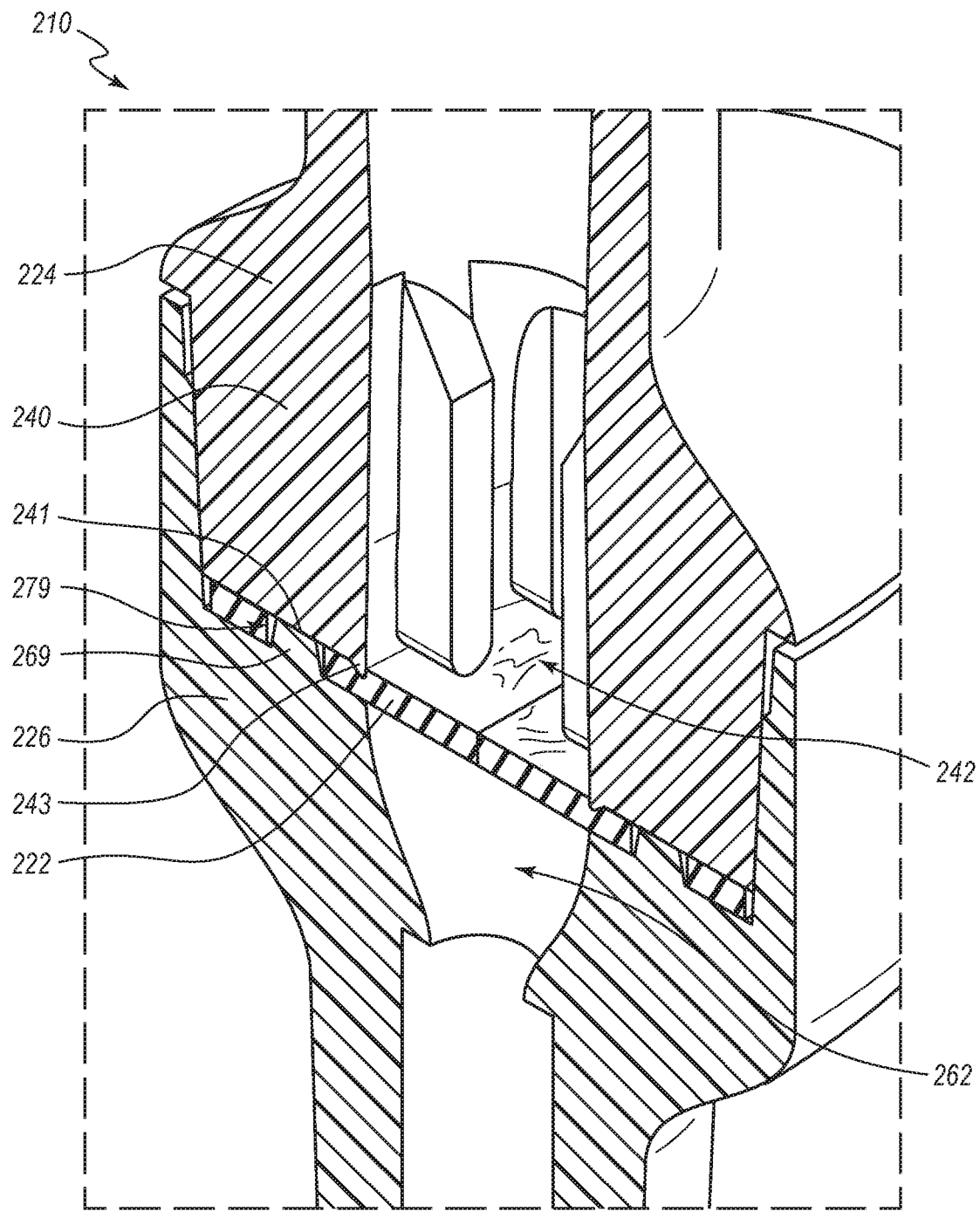
FIG. 30 is another cross-sectional perspective view of the valve of FIG. 19 taken along the view line 30-30 in FIG. 19.

With reference again to FIG. 29 and with additional reference to FIG. 30, when the valve 210 is in its assembled state, each post 269 of the distal housing member 226 extends through a separate channel 279 of the septum 222. A proximal surface of each post 269 can contact or abut against the distal face 241 of the sidewall 240 of the proximal housing member 224. The housing members 224, 226 can be securely attached together, such that each post 269 remains approximated to the sidewall 240 in this manner. A portion of the septum 222 thus is trapped between the housing members 224, 226 at an outward (e.g., radially or laterally outward) position relative to each post 269. These trapped portions of the septum 222 are incapable of moving around or in inwardly past the posts 269 when inwardly directed forces are applied to the septum 222 during infusion or aspiration. The posts 269 can cooperate with the channels 279 to secure the septum 222 relative to the housing. Stated otherwise, the posts 269 can prevent the septum 222 from being pulled fully into either of the chambers 242, 262 during aspiration or infusion, respectively, or stated otherwise, under the influence of pressurized fluid.

Alternative arrangements of the posts 269 are contemplated. For example, in other embodiments, the proximal housing member 226 can define the posts 269. In still other embodiments, each of the housing members 224, 226 can define one or more of the posts 269, such that some posts may project proximally while others may project distally. Such an arrangement could be advantageous from the perspective of tolerancing. For example, in the event that variations among the components were to yield gaps between one or more of the posts and an opposing housing surface, by having the posts 269 alternatively project proximally and distally, the septum 222 would still be unlikely to be both pulled over the top of one post and pulled under the bottom of an adjacent post. In still other embodiments, one housing member 224, 226 may include a post, and the opposing housing member 224, 226 can include a recess or a channel into which the post is receive.

With continued reference to FIGS. 29 and 30, the gripping rim 243 can impinge upon, embed in, or otherwise grip the septum 222, which opposition forces being provided by the opposing face 261 of the distal housing member 226. The gripping rim 243 can form the proximal and distal seals, as previously discussed, and can assist in preventing the septum 222 from being ingested into either of the chambers 242, 262. As shown in FIG. 30, the posts 269 can function as standoffs to ensure a desired spacing between the gripping rim 243 and the proximal face 261 is maintained. Stated otherwise, the posts 262 can prevent the housing members 224, 226 from being over-approximated to each other during manufacture. This can prevent over-compression of the septum 222, which could result in weakening, cutting, or tearing of the septum.

Figure 31:
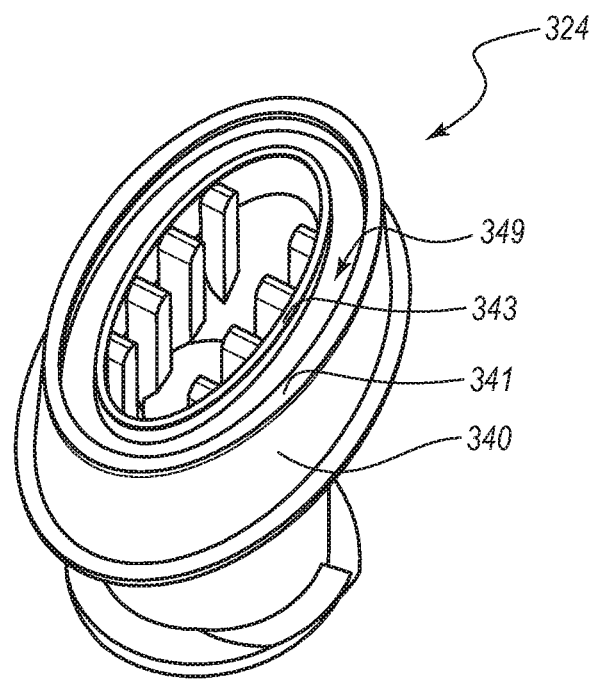
FIG. 31 is a bottom perspective view of another embodiment of first housing piece of another embodiment of a valve.
Figure 32:
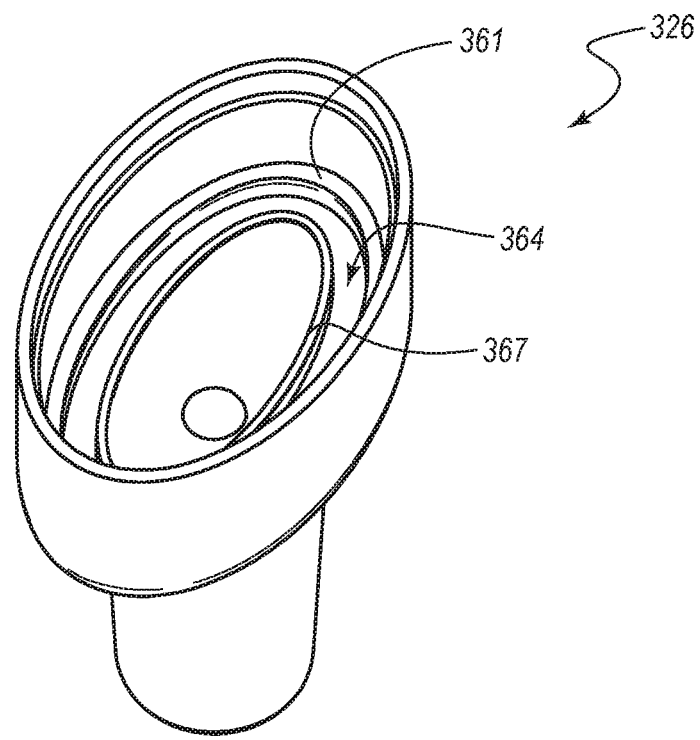
FIG. 32 is a top perspective view of an embodiment of a second housing piece that is compatible with the first housing piece of FIG. 31.
Figure 35:
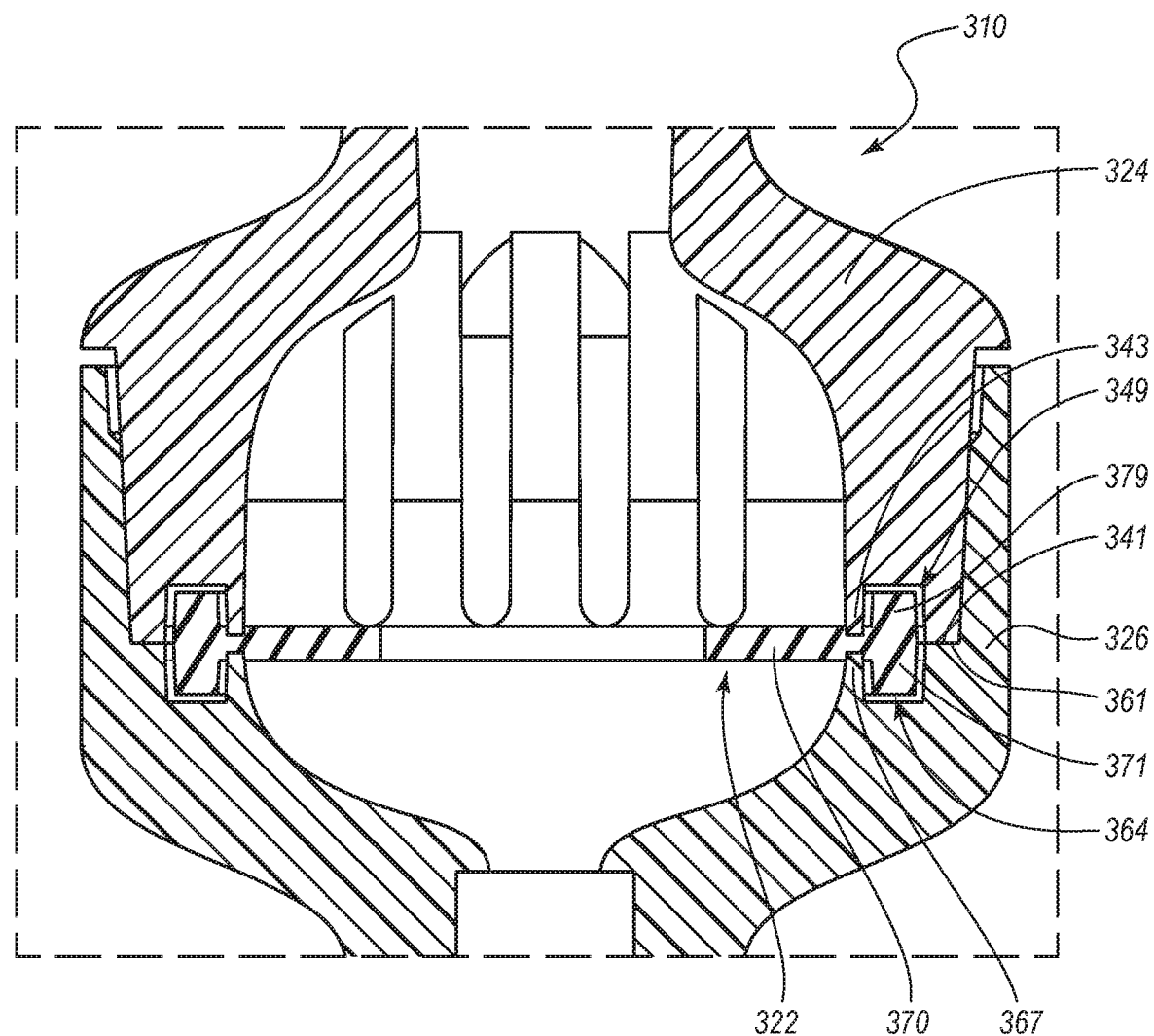
FIG. 35 is a cross-sectional view of a central portion of an embodiment of a valve that includes the first and second housing pieces of FIGS. 31 and 32 and the septum of FIG. 34.

FIGS. 31 and 32 depict proximal and distal housing members 324, 326, respectively, of another embodiment of a bi-directional valve 310 (see FIG. 35). As shown in FIG. 31, the proximal housing member 324 can include a sidewall 340 that defines a distal face 341 at an end thereof. The proximal housing member 324 can further define a groove 349 and a gripping rim 343. In the illustrated embodiment, the gripping rim 343 is shaped, in cross-section, substantially as an elongated trapezoid.

With reference to FIG. 32, the distal housing member 326 can include a groove 364 and a gripping rim 367. In the illustrated embodiment, the gripping rim 367 is shaped, in cross-section, substantially as an elongated trapezoid. The distal housing member 326 can further include a standoff or ledge 361, which extends about a full periphery of the housing member 326 in the illustrated embodiment. In other embodiments the ledge 361 can be discontinuous, or stated otherwise, a plurality of standoffs (e.g., ledges) may be distributed around the periphery of the housing member 326.

Figure 33:
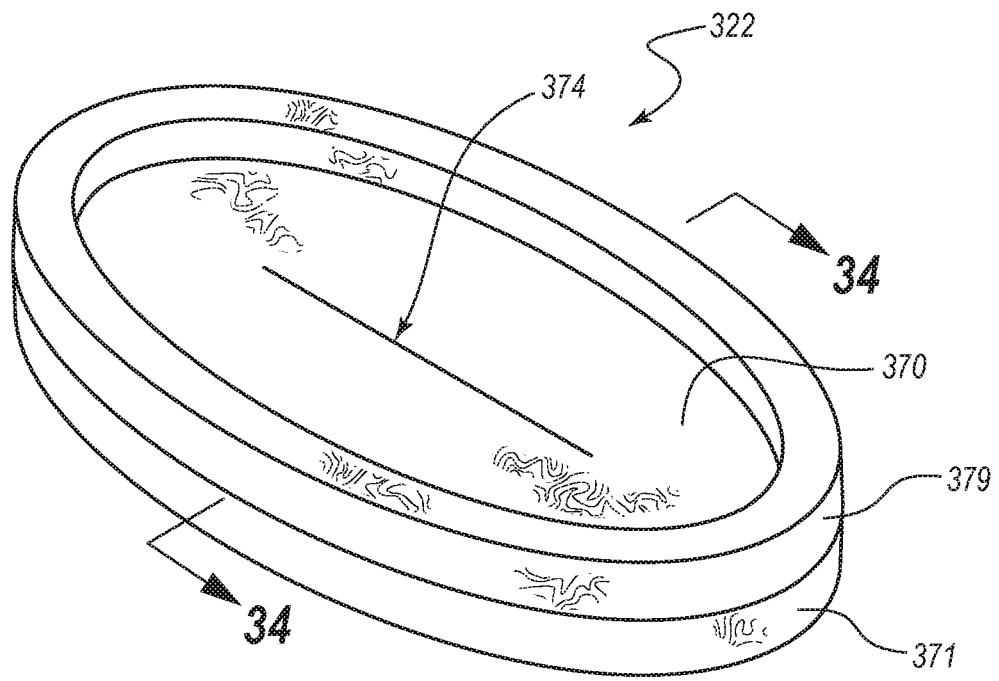
FIG. 33 is a perspective view of an embodiment of a septum that is compatible with the first and second housing pieces of FIGS. 31 and 32.
Figure 34:
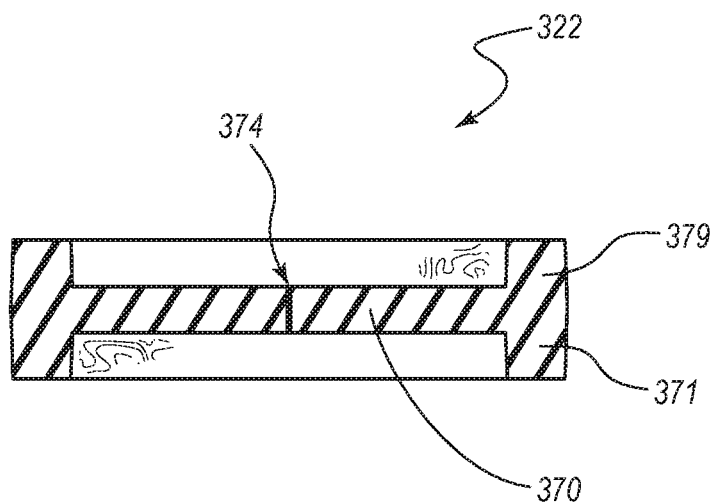
FIG. 34 is a cross-sectional view of the septum of FIG. 33 taken along the view lines 34-34 in FIG. 33.

With reference to FIGS. 33 and 34, in some embodiments, a septum 322 includes a main body 370 through which a selectively openable and closable, or sealable, closure 374 extends. As with the septum 122, the septum 322 includes a flange 371 that extends distally from the body 370. In the illustrated embodiment, the septum 322 further includes a second flange 379 that extends proximally from the body 370. The flanges 371, 379 may alternatively be considered as a single flange that extends about the full periphery of the body 370 in both the proximal and distal directions.

As shown in FIG. 35, the septum 322 can be captured between the proximal and distal housing members 324, 326 and thereby secured to the housing member 324, 326. In the illustrated embodiment, the proximal and distal gripping rims 343, 367 are aligned with each other and impinge on the body 370 of the septum 322 in opposite directions so as to squeeze the septum 322 therebetween. The proximal flange 379 of the septum 322 is received within the groove 349 and the distal flange 371 of the septum 322 is received within the groove 364. The flanges 379, 371 and the grooves 349, 364 can cooperate with each other to prevent ingestion of the septum 322 during aspiration or infusion. For example, when pressurized fluids act on the septum 322 to pull the periphery of the septum 322 inward, the flanges 379, 371 can abut against the outer surfaces of the gripping rims 343, 367, respectively. The gap between the gripping rims 343, 367 can be sufficiently small the prevent the flanges 379, 371 from passing therethrough, even when the septum 322 is stretched and/or distorted under the influence of pressurized fluids flowing through the septum 322.

Figure 36:
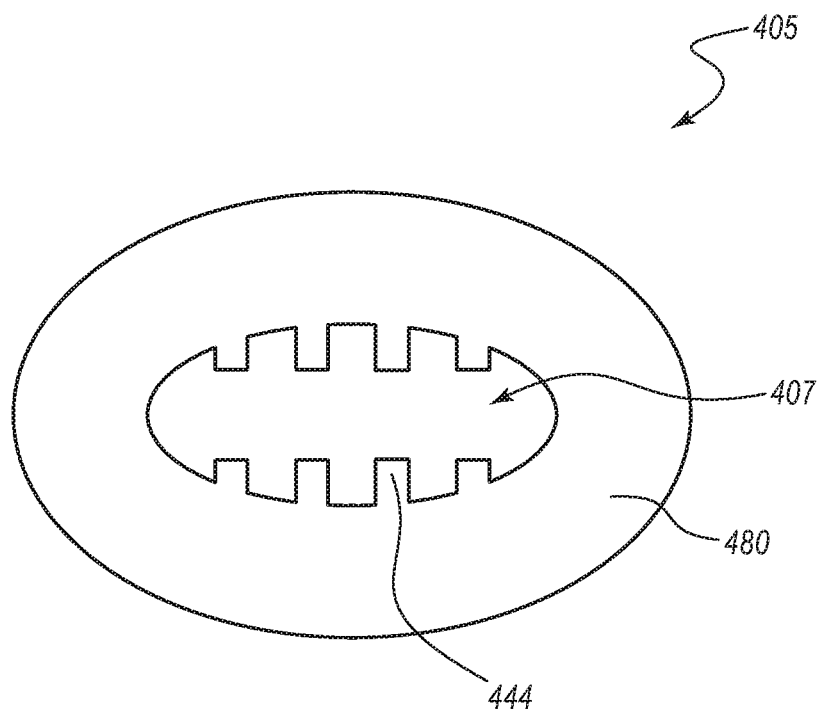
FIG. 36 is a top plan view of an embodiment of a projection plate that can be incorporated into another embodiment of a valve.
Figure 37:
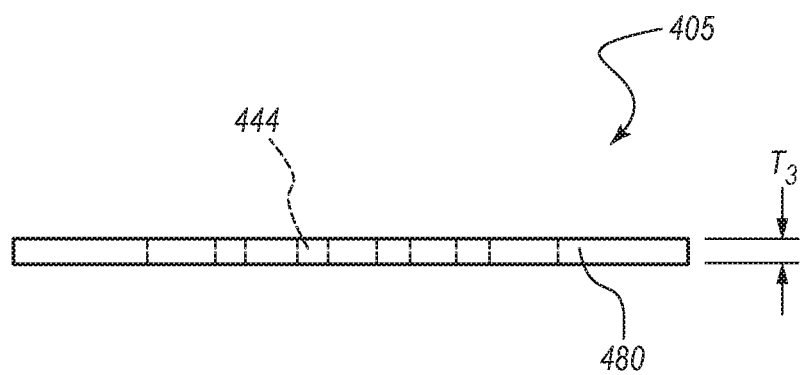
FIG. 37 is a side elevation view of the projection plate of FIG. 36.

FIGS. 36 and 37 depict an embodiment of a projection plate 405 that can be incorporated into certain embodiments of bi-directional valves. For example, the projection plate 405 can be incorporated into embodiments of the valves 110, 210, 310.

The projection plate 405 can comprise a body 480 from which a plurality of projections 444 extend inwardly into an opening 407. The opening 407 can extend fully through the body 480. The projections 444 can define a profile similar to the plan-view profile of other embodiments. For example, the projection plate 405 can have a similar profile to the bottom plan view of the proximal housing member 224, as depicted in FIG. 23.

The projections 444 can replace other projection features previously disclosed. By way of example, in some embodiments, the fins 244 of the proximal housing member 224 (e.g., of FIGS. 21-23) can be omitted, and the projection plate 405 can instead be incorporated into the valve 210 by being placed between the proximal surface of the septum 222 and the distal face 241 of the proximal housing member 224.

Stated otherwise, in some embodiments of the valves 110, 210, 310, the illustrated fins can be omitted and replaced with the projection plate 405. The projections 444 can function substantially in the same manner as the bottom ends of the fins, as previously disclosed. In some embodiments, the plate 405 can be securely attached to the proximal housing member in an early stage of assembly—e.g., prior to coupling the proximal housing member to the septum and the distal housing member.

As shown in FIG. 37, in some embodiments, the projection plate 405 defines a thickness $T_3$. In various embodiments, composition of the projection plate 405 and/or the thickness $T_3$ may be sufficient to prevent or inhibit the projections 444 from bending, either distally or proximally, during infusion or aspiration, respectively. In various embodiments, the projection plate 405 includes one or more of metallic or polymeric materials. In some embodiments, the projection plate 405 is formed of a sheet metal, such as a sheet of stainless steel. In other embodiments, the projection plate 405 comprises a metalized plastic (e.g., a plastic sheet coated in metal). In some instances, inclusion of a metallic material may provide advantageous antimicrobial properties.

In the illustrated embodiment, the tips of the projections 444 have a rectangular profile. In other embodiments, the tips of one or more of the projections 444 may have a rounded or smooth profile. In some embodiments, all edges of the projection plate may be smoothed.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order.

It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. For example, although FIGS. 6 and 9 have been referred to as bottom and top views, respectively, these orientations are merely expressed with respect to the orientation of the valve depicted in FIG. 2. In various embodiments, the valve may be operated with the valve in any orientation (e.g., independent of whether the luer fitting is "up" or "down" relative to a gravitational influences). The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A medical valve comprising:
   a housing comprising a sidewall and defining a chamber;
   a connection interface in fluid communication with the chamber, the connection interface being configured to couple with one or more medical devices for infusion of fluid through the medical valve in a distal direction and aspiration of fluid through the medical valve in a proximal direction;
   a septum coupled to the housing, the septum comprising a proximal surface, a distal surface, and a selectively openable closure that extends through a full thickness of the septum between the proximal surface and the distal surface, wherein the closure is positioned within the chamber; and
   a plurality of projections that extend away from the sidewall, each projection comprising a restriction surface at a distal end thereof that is configured to contact the proximal surface of the septum to oppose movement of a restricted portion of the septum in the proximal direction such that an aspiration cracking pressure required to open the closure to permit fluid flow through the septum in the proximal direction exceeds an infusion cracking pressure required to open the closure to permit fluid flow through the septum in the distal direction,
   wherein the proximal surface of the septum further comprises contact regions at which the septum is configured to contact the restriction surfaces of the plurality of projections,
   wherein the restricted portion of the septum defines an area that comprises the contact regions, and
   wherein a collective total area of the contact regions of the septum is smaller than the area of the restricted portion of the septum.

2. The medical valve of claim 1, wherein the plurality of projections are configured to permit free movement of the restricted portion of the septum in the distal direction.

3. The medical valve of claim 1, wherein the plurality of projections are positioned exclusively at one of two opposing sides of the septum.

4. The medical valve of claim 1, wherein the collective total area of the contact regions of the septum is no greater than 50 percent of the area of the restricted portion of the septum.

5. The medical valve of claim 1, wherein.

6. The medical valve of claim 1, wherein the restriction surfaces of the plurality of projections are configured to separately contact different regions of the restricted portion of the septum.

7. The medical valve of claim 1, wherein the sidewall of the housing defines an outer perimeter of a primary active region of the septum, wherein the restricted portion of the septum and the sidewall cooperate to define an outer perimeter of a secondary active region of the septum, and wherein the primary active region of the septum is larger than the secondary active region.

8. The medical valve of claim 1, wherein the plurality of projections are arranged in distinct groups positioned at opposite sides of the closure of the septum, and
   wherein, within each distinct group of projections, pairs of adjacent projections define flushing channels through which a fluid can flow to flush contact surfaces of the projections when the fluid passes through the valve in the distal direction.

9. The medical valve of claim 1, wherein the septum is sufficiently compliant to move away from the plurality of projections in the distal direction by a sufficient amount to permit fluid to pass between the plurality of projections and the septum such that substantially all of the proximal surface of the septum is flushed during infusion of fluid through the valve in the distal direction.

10. The medical valve of claim 1, wherein the housing defines the projections.

11. The medical valve of claim 1, wherein a unitary piece of material is integrally formed to define the projections and at least a portion of the housing.

12. The medical valve of claim 1, wherein the plurality of projections are coupled to only one of the two housing pieces.

13. The medical valve of claim 1, wherein the housing comprises a gripping rim configured to compress a portion of the septum.

14. The medical valve of claim 1, wherein the housing defines a groove and the septum defines a flange that fits within the groove, and wherein the groove and the flange cooperate to prevent the septum from being pulled fully into the chamber and out of secure attachment from the housing under the influence of pressurized fluid.

15. The medical valve of claim 1, wherein the septum comprises a plurality of channels about a periphery thereof and the housing comprises a plurality of posts, and wherein each post of the plurality of posts extends through a separate channel of the plurality of channels to secure the septum relative to the housing.

16. The medical valve of claim 1, wherein the plurality of projections comprises a plurality of fins.

17. The medical valve of claim 16, wherein each fin of the plurality of fins extends longitudinally.

18. The medical valve of claim 1, further comprising a plate that defines the projections.

19. A medical valve comprising:
   a housing comprising a sidewall that defines at least a portion of a chamber;
   a septum fixedly secured to the housing and comprising a selectively openable closure; and
   a plurality of restriction surfaces positioned inward of the sidewall within the chamber and adjacent to a proximal face of the septum, the restriction surfaces being configured to press against the proximal face of the septum to delimit movement of a portion of the septum when the septum is urged in a first direction toward the restriction surfaces and further being configured to permit free movement of the septum away from the restriction surfaces when the septum is urged in a second direction away from the restriction surfaces, such that the closure is more difficult to open when the septum is urged in the first direction as compared to when the septum is urged in the second direction, wherein each of the restriction surfaces narrows in a distal direction to a distal end such that only a small portion thereof contacts the proximal face of the septum.

20. The medical valve of claim 19, wherein each distal end of the restriction surfaces is curved.

21. The medical valve of claim 19, wherein each restriction surface is shaped substantially as a hemicylinder or is formed of two planar surfaces that meet at a line that extends along a lower edge of the restriction surface.

22. The medical valve of claim 19, wherein each restriction surface defines a substantially semicircular cross-section, a substantially U-shaped cross-section, or a substantially V-shaped cross-section.

23. A medical valve comprising:

a housing comprising a sidewall that defines at least a portion of a chamber;

a septum coupled to the housing and comprising a selectively openable closure that is positioned within the chamber; and support structures extending inwardly from the sidewall, the of support structures comprising restriction surfaces positioned adjacent to the septum, the restriction surfaces being configured to press against the septum to delimit movement of a portion of the septum when the septum is urged in a first direction toward the restriction surfaces and further being configured to permit movement of the septum away from the restriction surfaces when the septum is urged in a second direction away from the restriction surfaces, wherein the septum is configured to move away from the restriction surfaces by an amount sufficient to permit fluid to pass between the septum and the restriction surfaces to thereby flush the restriction surfaces, and wherein the closure exhibits a first cracking pressure when the septum is urged in the first direction and exhibits a second cracking pressure that is lower than the first cracking pressure when the septum is urged in the second direction, wherein the support structures are arranged in a first group comprising a first plurality of support structures positioned at a first side of the closure and a second group comprising a second plurality of support structures positioned at a second side of the closure opposite the first side, the first and second groups being distinct from each other.

24. The medical valve of claim 23, wherein the first plurality of support structures defines one or more flushing channels, and wherein each flushing channel is defined, in part, by opposing faces of adjacent support structures.

* * * * *